(12) United States Patent
Carlson et al.

(10) Patent No.: US 9,212,245 B2
(45) Date of Patent: Dec. 15, 2015

(54) HIGH PERFORMANCE ACRYLAMIDE ADHESIVES

(71) Applicant: Empire Technology Development LLC, Wilmington, DE (US)

(72) Inventors: William B. Carlson, Seattle, WA (US); Gregory D. Phelan, Cortland, NY (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 182 days.

(21) Appl. No.: 13/980,535

(22) PCT Filed: Dec. 4, 2012

(86) PCT No.: PCT/US2012/067765
§ 371 (c)(1),
(2) Date: Jul. 18, 2013

(87) PCT Pub. No.: WO2014/088555
PCT Pub. Date: Jun. 12, 2014

(65) Prior Publication Data
US 2014/0155563 A1    Jun. 5, 2014

(51) Int. Cl.
| | | |
|---|---|---|
| C08F 24/00 | (2006.01) |
| C07H 3/02 | (2006.01) |
| C07H 15/12 | (2006.01) |
| C08F 220/58 | (2006.01) |
| C07H 13/04 | (2006.01) |
| C07H 15/04 | (2006.01) |
| C08F 222/38 | (2006.01) |

(52) U.S. Cl.
CPC .............. *C08F 220/58* (2013.01); *C07H 13/04* (2013.01); *C07H 15/04* (2013.01); *C08F 222/385* (2013.01)

(58) Field of Classification Search
CPC ...... C07H 13/04; C07H 15/04; C08F 220/58; C08F 222/385
USPC ............... 526/303.1, 238.23; 536/29.1, 53
See application file for complete search history.

(56) References Cited

U.S. PATENT DOCUMENTS

| | | |
|---|---|---|
| 3,153,593 A | 10/1964 | De Pauw |
| 3,542,908 A | 11/1970 | Sharples et al. |
| 4,156,777 A | 5/1979 | Kimura |
| 4,323,487 A | 4/1982 | Jones et al. |
| 4,476,593 A | 10/1984 | Fanselow et al. |
| 4,587,331 A | 5/1986 | Hlavka et al. |
| 4,601,757 A | 7/1986 | Brown et al. |
| 4,771,105 A | 9/1988 | Shirai et al. |
| 4,822,848 A | 4/1989 | Ito et al. |
| 4,865,640 A | 9/1989 | Avera |
| 4,996,059 A | 2/1991 | Grollier et al. |
| 5,002,680 A | 3/1991 | Schmidt et al. |
| 5,045,617 A | 9/1991 | Shih et al. |
| 5,232,688 A | 8/1993 | Ziegler et al. |
| 5,294,435 A | 3/1994 | Remz et al. |
| 5,474,768 A | 12/1995 | Robinson |
| 5,609,862 A | 3/1997 | Chen et al. |
| 5,646,100 A | 7/1997 | Haugk et al. |
| 5,698,052 A | 12/1997 | Russo et al. |
| 5,965,147 A | 10/1999 | Steffier |
| 5,993,857 A | 11/1999 | Menzel et al. |
| 6,133,212 A | 10/2000 | Elliott et al. |
| 6,277,892 B1 | 8/2001 | Deckner et al. |
| 6,410,668 B1 | 6/2002 | Chiari |
| 6,488,091 B1 | 12/2002 | Weaver et al. |
| 6,552,103 B1 | 4/2003 | Bertozzi et al. |
| 6,613,378 B1 | 9/2003 | Erhan et al. |
| 6,664,356 B1 | 12/2003 | Shih |
| 6,875,426 B2 | 4/2005 | Candau |
| 7,422,735 B1 | 9/2008 | Hossel et al. |
| 7,423,090 B2 | 9/2008 | Doane et al. |
| 7,455,848 B2 | 11/2008 | Hessefort et al. |
| 7,541,414 B2 | 6/2009 | Lion |
| 7,560,428 B2 | 7/2009 | Hirai et al. |
| 7,597,879 B2 | 10/2009 | Gupta |
| 7,601,340 B2 | 10/2009 | Nojiri et al. |
| 7,671,007 B2 | 3/2010 | Carnali et al. |
| 7,754,192 B2 | 7/2010 | Wood et al. |
| 7,763,240 B2 | 7/2010 | Anderson et al. |
| 7,777,073 B2 | 8/2010 | Gupta |
| 7,780,954 B2 | 8/2010 | Polonka et al. |
| 7,785,575 B2 | 8/2010 | Anderson et al. |
| 7,794,839 B2 | 9/2010 | Schmidt et al. |
| 7,875,264 B2 | 1/2011 | Takakura et al. |
| 8,017,553 B2 | 9/2011 | Doane et al. |

(Continued)

FOREIGN PATENT DOCUMENTS

| | | |
|---|---|---|
| BE | 603491 | 5/1961 |
| CN | 101438701 | 5/2009 |

(Continued)

OTHER PUBLICATIONS

Non-Final Office Action in U.S. Appl. No. 13/879,976 dtd Jan. 30, 2015 (18 pages).
Non-Final Office Action in U.S. Appl. No. 13/946,710 dtd Feb. 24, 2015 (7 pages).
Bahulekar, R. et al., "Polyacrylamide containing sugar residues: synthesis, characterization and cell compatibility studies," Carbohydrate Polymers, vol. 37, 1998, pp. 71-78.
Bird, T.P., et al, "Polyamides Containing Carbohydrate Residues. II. Benzylidenedioxy derivatives," Journal of the Chemical Society, 1963, pp. 3389-3391.
Bird, T.P., et al, "Preparation and Derivatives of Poly-(6-O-methacryloyl-D-galactose) and Poly-(6-O-acryloyl-D-galactose)," Journal of the Chemical Society (C), vol. 21, 1966, pp. 1913-1918.

(Continued)

*Primary Examiner* — Ling Choi
*Assistant Examiner* — Chun-Cheng Wang
(74) *Attorney, Agent, or Firm* — Foley & Lardner LLP

(57) ABSTRACT

Disclosed are derivatives of (tetrahydropyranyl)methyl acrylamide and polymers derived therefrom, as well as methods of making such compounds and polymers. Adhesives, coatings, and plastics which include such polymers are also described.

17 Claims, 4 Drawing Sheets

(56) References Cited

U.S. PATENT DOCUMENTS

| | | |
|---|---|---|
| 8,316,580 B2 | 11/2012 | Krysiak et al. |
| 2002/0111281 A1 | 8/2002 | Vishnupad |
| 2002/0128346 A1 | 9/2002 | Domschke et al. |
| 2002/0150688 A1 | 10/2002 | Knight et al. |
| 2006/0035341 A1 | 2/2006 | Boeckh et al. |
| 2006/0113080 A1 | 6/2006 | Nguyen et al. |
| 2007/0031366 A1 | 2/2007 | Meyers et al. |
| 2007/0107638 A1 | 5/2007 | Chun et al. |
| 2008/0057206 A1 | 3/2008 | Igo et al. |
| 2008/0066509 A1 | 3/2008 | Turley |
| 2008/0281064 A1 | 11/2008 | Chiron et al. |
| 2009/0026338 A1 | 1/2009 | Bruce |
| 2009/0074823 A1 | 3/2009 | Takaura |
| 2009/0137771 A1 | 5/2009 | Moriyama et al. |
| 2009/0263338 A1 | 10/2009 | Rolland et al. |
| 2009/0297466 A1 | 12/2009 | Gutmann et al. |
| 2010/0003236 A1 | 1/2010 | Dalko et al. |
| 2010/0028284 A1 | 2/2010 | Atis et al. |
| 2010/0028285 A1 | 2/2010 | Frampton et al. |
| 2010/0074855 A1 | 3/2010 | Tanaka et al. |
| 2010/0090160 A1 | 4/2010 | Branning |
| 2010/0093535 A1 | 4/2010 | Rose et al. |
| 2010/0218781 A1 | 9/2010 | McNamara et al. |
| 2010/0275664 A1 | 11/2010 | Windhoevel |
| 2010/0291055 A1 | 11/2010 | Athanasiadis et al. |
| 2011/0028607 A1 | 2/2011 | Morgan et al. |
| 2011/0275577 A1 | 11/2011 | Priebe et al. |
| 2011/0282048 A1 | 11/2011 | Brumer et al. |
| 2012/0220454 A1 | 8/2012 | Chen et al. |
| 2012/0277099 A1 | 11/2012 | Olson et al. |
| 2014/0178344 A1 | 6/2014 | Carlson et al. |

FOREIGN PATENT DOCUMENTS

| | | | |
|---|---|---|---|
| CN | 102511480 | 6/2012 | |
| CN | 101723765 | 11/2012 | |
| CZ | 278551 | 1/1994 | |
| CZ | 8500097 | 1/1994 | |
| DE | 11 54 815 | 9/1963 | |
| DE | 28 05 185 | 7/1978 | |
| EP | 0 186 085 | 7/1986 | |
| EP | 0 608 353 | 8/1994 | |
| EP | 1 516 612 | 3/2005 | |
| EP | 1 704 769 | 9/2006 | |
| EP | 1 820 490 | 8/2007 | |
| GB | 0 935 290 | 8/1963 | |
| GB | 1 099 372 | 1/1968 | |
| JP | 57-202309 | 12/1982 | |
| JP | 57202309 A * | 12/1982 | ............ C08F 120/58 |
| JP | 63-280001 | 11/1988 | |
| JP | 2007-206166 | 8/2007 | |
| JP | 2009-175875 | 8/2009 | |
| JP | 05-056707 | 10/2012 | |
| WO | WO-91/05459 | 5/1991 | |
| WO | WO-93/07856 | 4/1993 | |
| WO | WO-99/64563 | 12/1999 | |
| WO | WO 9964563 * | 12/1999 | ............ C08F 20/06 |
| WO | WO-2004/028686 | 4/2004 | |
| WO | WO-2008/132340 | 11/2008 | |
| WO | WO-2012/022164 | 2/2012 | |

OTHER PUBLICATIONS

Black, W.A.P. et al., "6-O-Methacryloyl-D-galactose: a reactive, water-soluble monomer," Die Makromolekulare Chemie, vol. 117, 1968, pp. 210-214.

Bock, K., et al, "Amino Acids and Amino Sugars from Bromodeoxyaldonolactones," Acta Chemica Scandinavica, B, vol. 41, 1987, pp. 435-441.

Botto, R.E., et al, "Nitrogen-15 Nuclear Magnetic Resonance Spectroscopy of Neomycin B and Related Aminoglycosides," Journal of the American Chemical Society, vol. 105, No. 4, 1983, pp. 1021-1028.

Brendel, K. et al., "Amino sugar synthesis. XIII. Mechanism of nucleophilic replacement of methanesulfonyl groups—simultaneous formation of D-gulosamine and D-galactosamine derivatives from D-glucosamine derivatives," Justus Liebigs Annalen der Chemie, vol. 683, 1965, pp. 182-186. (English Translation Not Available).

Brendel, K. et al., "Preparation of 2,6-diamino-2,6-dideoxy-D-arabino-hexose. An improved preparation of benzyl 3,4-di-O-acetyl-2-[(benzyloxycarbonyl)amino] -2-deoxy -α-D-glucurononitrile," Chemische Berichte, vol. 97, No. 5, 1964, pp. 1513. (English Translation Not Available).

Brendel, K., et al., "2-Amino-2.6-didesoxy-D-allose und 2-Amino2. 6-didesoxy-Dglucose," Aminozuckersynthesen, XVI, 1966 pp. 192-197. (English Translation Not Available).

Brimacombe, J.S., et al, "A convenient synthesis of 2,6-diamino-2,6-dideoxy-D-gulose," Carbohydrate Research, vol. 25, 1972, pp. 522-525.

Chen, S. et al., "Synthesis of melamine-glucose resin adhesive," Science in China Series B: Chemistry, vol. 48, 2005, pp. 29-32.

Christiansen, A.W. et al., "Potential of carbohydrates for exterior-type adhesives," Forrest Products Journal, vol. 36, No. 7/8, Jul./Aug. 1986, pp. 20-28.

Collins, P.M., et al, "The Synthesis of Amino-sugars from Glycopyranosiduloses," Journal of the Chemical Society, 1965, pp. 3448-3456.

Dorn, H. et al., "Potential cytostats. V," Monatsberichte der Deutschen Akademie der Wissenschaften zu Berlin, vol. 6, No. 6, 1964, pp. 447-454. (English Translation Not Available).

Dos Santos, L.A., et al, "Dual-Setting Calcium Phosphate Cement Modified with Ammonium Polyacrylate," Artificial Organs, vol. 27, No. 5, 2003, pp. 412-418.

Dyer, J.R., et al, "Streptomycin. II. Streptose," Journal of the American Chemical Society, vol. 87, No. 3, Feb. 5, 1965, pp. 654-655.

Fatiadi, A.J., et al, "Cyclic Polyhydroxy Ketones II. xylo-Trihydroxycyclohexenediolic Acid and Keto-Inositols," Journal of Research of the National Bureau of Standards, Section A: Physics and Chemistry, vol. 68A, No. 3, May-Jun. 1964, pp. 287-299.

Goda, S.K., et al., "Neomycin Biosynthesis: The Incorporation of D-6-Deoxy-Glucose Derivatives and Variously Labelled Glucose into the 2-Deoxystreptamine Ring: Postulated Involvement of 2-Deoxyinosose Synthase in the Biosynthesis," The Journal of Antibiotics, vol. 45, No. 6, Jun. 1992, pp. 984-994.

Granville, A.M., et al, "Chemo-enzymatic Synthesis and RAFT Polymerization of 6-O-Methacryloyl Mannose: A Suitable Glycopolymer for Binding to the Tetrameric Lectin Concanavalin A?," Macromol. Symp., vol. 255, 2007, pp. 81-89.

Gross, P.H., et al., "Amino sugar synthesis. XVII. Synthesis of D-rhamnosamine and of 2,6-diamino-2,6-dideoxy-D-mannose from N-acetyl-D-mannosamine," Justus Liebigs Annalen der Chemie, vol. 691, 1966, pp. 198-204. (English Translation Not Available).

Gross, P.H., et al., "Amino sugar synthesis. XII. 2,6-Diamino-2,6-dideoxy-D-allose," Justus Liebigs Annalen der Chemie, vol. 683, 1965, pp. 179-182. (English Translation Not Available).

Gross, P.H. , et al., "2,6-Diamino-2,6-dideoxy-D-mannose and D-rhamnosamine from D-glucosamine," Naturwissenschaften, vol. 52, No. 8, 1965, pp. 185.

Gross, P.H. et al., "Amino sugar syntheses. IX. Synthesis of 2,6-diamino-2,6-dideoxy-D-gulose by using an oxazolidone protective group," Justus Liebigs Annalen der Chemie, vol. 681, 1965, pp. 225-227. (English Translation Not Available).

Gross, P.H. et al., "2,6-Diamino-2,6-dideoxy-D-allose from glucosamine by use of an inversion with thionyl chloride," Die Naturwissenschaften, vol. 51, No. 21, 1964, pp. 509-510.

Gross, P.H. et al., "New oxazolidone synthesis and preparation of 2,6-diamino-2,6-dideoxy-D-gulose," Angewandte Chemie, vol. 76, No. 9, 1964, pp. 377. (English Translation Not Available).

Haskell, T.H., et al, "Paromomycin II. Paromobiosamine, A Diaminohexosyl-D-Ribose," Journal of the American Chemical Society, vol. 81, Jul. 5, 1959, pp. 3481.

Haskell, T.H., et al, "Paromomycin. I. Paromamine, a glycoside of D-glucosamine," Journal of the American Chemical Society, vol. 81, Jul. 5, 1959, pp. 3480-3481.

Haskell, T.H., et al, "The Configuration of Paromose," Journal of Organic Chemistry, vol. 28, Oct. 1963, pp. 2598-2604.

(56) References Cited

OTHER PUBLICATIONS

Horii, S., et al. "Separation of zygomycin A1 and zygomycin A2 and their degradation products," Takeda Kenkyusho Nenpo, vol. 23, 1964, pp. 8-17.

Huettenrauch, R. et al., "Detection of the primary cleavage products of paromomycin," Pharmazeutische Zentralhalle fuer Deutschland, vol. 104, No. 2, 1965, pp. 85-87. English Translation Not Available.

International Search Report and Written Opinion received for PCT/US2012/063261 dated Jan. 22, 2013, 11 pp.

International Search Report and Written Opinion received for PCT/US12/67765 dated Feb. 26, 2013.

Kadokawa, J., et al, "Synthesis of new aminopolysaccharides by polymerization of 6-amino-6-deoxy-D-glucose and 2,6-dideoxy-D-glucose," European Polymer Journal, vol. 36, 2000, pp. 225-230.

Kakinuma, K., et al, "Mechanism and Stereochemistry of the Biosynthesis of 2-Deoxystreptamine and Neosamine C," The Journal of Antibiotics, Jun. 1989, pp. 926-933.

Kakinuma, K., et al., "Sterochemistry of Ribostamycin Biosynthesis. An Application of 2H NMR Spectroscopy," Journal of American Chemical Society, vol. 103, No. 18, 1981, pp. 5614-5616.

Kakinuma, K., et al, "Transamination Stereochemistry in the Formation of Neosamine C of Ribostamycin," The Journal of Antibiotics, vol. 36, No. 6, Jun. 1983 pp. 749-750.

Kakinuma, K., et al, "Stereochemistry of ribostamycin biosynthesis studied by deuterium NMR spectroscopy," Tennen Yuki Kagobutsu Toronkai Koen Yoshishu, vol. 24,1981, pp. 537-544. English Translation Not Available.

Kim, S. et al., "Design of new biomimetic glycopolymers for hepatocellular engineering," Proceedings of the International Symposium on Controlled Release of Bioactive Materials, 27th, 2000, pp. 638-639.

Komor, E. et al., "Sugar specificity and sugar-proton interaction for the hexose-proton-symport system of Chlorella," European Journal of Biochemistry, vol. 146, 1985, pp. 649-656.

Konishi, M. et al., "Aminoglycoside antibiotics. VI. Structure determination of 4'-deoxybutirosins (Bu-1975C1 and C2)," The Journal of Antibiotics, vol. 27, No. 6, Jun. 1974, pp. 471-483.

Koster, H. et al., "Physiology and biochemistry of streptomycetes. XI. Different incorporation of D-glucose-u-14C into the paromomycin isomers and the precursors of paromomycin I," Zeitschrift fuer Allgemeine Mikrobiologie, vol. 17, No. 6, 1977, pp. 433-436. English Abstract Only.

Krul, L.P. et al., "Water-Soluble Polymers of Acrylamide as Labeling Adhesives," Russian Journal of applied Chemistry, vol. 78, No. 5, 2005, pp. 856-859.

Kurita, K. et al., "Synthetic polymers containing sugar residues, 8. Novel polyureas from 2,6-diamino-2,6-dideoxy-d-gulose and diisocyanates," Die Makromolekulare Chemie, vol. 187, Jun. 1986, pp. 1359-1365.

Kuzyaeva, V.A., "Degradation products of colimycin, mycerin, and neomycin," Antibiotiki (Moscow), vol. 9, No. 9, 1964, pp. 784-788.—English Translation Not Available.

Liebermann, B. et al., "Physiology and biochemistry of Streptomycetes. 12. Different uptake and utilization of radioactive-labeled dendrolites of paromomycin by Streptomyces albus var. metamycinus novus var," Pharmazie, vol. 32, May 1977, pp. 293-295.

Lodhi, S., et al, "Interactions of Neomycin and Calcium in Synaptosomal Membranes and Polyphosphoinositide Monolayers," Biochimica et Biophysica Acta, vol. 426, 1976, pp. 781-785.

Ludowieg, J.J., et al, "A Method for Analysis of Amino Sugars: Specificity and Mechanism of the Reaction," Carbohydrate Research, vol. 8, 1968, pp. 185-192.

Meyer Zu Reckendorf, W. et al., "Di- and polyaminozucker, XIX N-(2.4-dinitrophenyl)-derivate von diamino-didesoxy-hexosen," Tetrahedron Letters, vol. 13, No. 33, 1972, pp. 3461-3464. (English Translation Not Available).

Meyer Zu Reckendorf, W. et al., "Diamino sugars. VII. New syntheses of 2,6-diamino-2,6-dideoxy-D-allose," Chemische Berichte, vol. 101, No. 7, 1968, pp. 2289-2293. (English Translation Not Available).

Meyer Zu Reckendorf, W. "Diaminosugars—IV. The Synthesis of 2,6-diamino-2,6-Dideoxy-L-Idose," Tetrahedron, vol. 19, 1963, pp. 2033-2038.

Meyer Zu Reckendorf, W., "2,6-Diamino-2,6-dideoxy-β-D-mannose. From methyl 2-benzamido-4,6-O-benzylidene-2-deoxy-α-Daltropyranoside by inversion at C-3 via neighboring group participation," Methods in Carbohydrate Chemistry, vol. 6, 1972, pp. 274-276.

Meyer Zu Reckendorf, W., "2,6-Diamino-2,6-dideoxy-α-D-galactose. From methyl 2,6-bis(benzamido)-2,6-dideoxy-3-O-methyl-4-Omethylsulfonyl-62-D-glucopyranoside by inversion at C-4 via neighboring group participation," Methods in Carbohydrate Chemistry, vol. 6, 1972, pp. 270-273.

Meyer Zu Reckendorf, W., et al, "A large-scale synthesis of 2,6-diamino-2,6-dideoxy-D-glucose," Carbohydrate Research, vol. 45, 1975, pp. 307-311.

Meyer Zu Reckendorf, W., "Synthesis of 2,6-diamino-2,5-dideoxy-β-D-mannose. A derivative of 2,6-imino-2,6-dideoxy-α-D-altrose," Chemische Berichte, vol. 98, No. 1, 1965, pp. 93-97. (English Translation Not Available).

Meyer Zu Reckendorf, W., "Diamino sugars. V. Synthesis of 2,3-diamino-2,3-dideoxy-D-allose, 2,3-diamino-2,3-dideoxy-α-D-glucose, and 2,6-diamino-2,6-dideoxy-α-D-allose," Chemische Berichte, vol. 97, No. 5, 1964, pp. 1275-1285. (English Translation Not Available).

Meyer Zu Reckendorf, W., "Diamino sugars. II. Synthesis of 2,6-diamino-2,6-dideoxy-D-galactose," Chemische Berichte, vol. 96, No. 8, 1963, pp. 2019-2023. (English Translation Not Available).

Meyer Zu Reckendorf, W., "Synthesis of 2,6-diamino-2,6-dideoxy-L-idose," Angewandte Chemie, vol. 75, 1963, pp. 573. (English Translation Not Available).

Meyer Zu Reckendorf, W., "Diamino sugars. I. A simple synthesis of 2,6-diamino-2,6-dideoxy-β-D-glucose," Chemische Berichte, vol. 96, 1963, pp. 2017-2018. (English Translation Not Available).

Meyer Zu Reckendorf, W. et al., "Di- und Polyaminozucker, XVIII Synthesen der 2.4-Diamino-2.4-didesoxy-D-galaktose und -D-glucose," Chemische Berichte, vol. 105, 1972, pp. 2998-3014. (English Translation Not Available).

Miyake, A. et al., "Zygomycins, antibiotic substances produced by Streptomyces pulveraceus," Takeda Kenkyusho Nenpo, vol. 23, 1964, pp. 209-236.

Morris, J.C., et al, "Role of 2,6-Dideoxy-2,6-diaminoglucose in Activation of a Eukaryotic Phospholipase C by Aminoglycoside Antibiotics," The Journal of Biological Chemistry, vol. 272, No. 47, Nov. 21, 1997, pp. 29554-29559.

Nakanishi, G. et al., "Thermosetting Adhesive Based on Tannin and Poly(NHydroxymethyl Acrylamide)," The Journal of Adhesion, vol. 84, No. 7, 2008, pp. 638-652.

Ogawa, S., et al, "Chemistry of the Neomycins. XIII. Synthesis of Aminocyclitols and Amino Sugars via Nitromethane Condensations," Journal of Organic Chemistry, vol. 39, No. 6, 1974, pp. 812-821.

Ohnsmann, J., "Selective deblockable 2,6-diamino-2,6-didesoxy-D-glucose-Scaffolds for the combinatorial synthesis of potential RNA ligands," Dissertation, Oct. 9, 2006, 244 pgs. (English Abstract Only).

Onodera, K., et al, "The Amadori Rearrangement Product as an Intermediate in the Browning Reaction—Part I. Preparation and Infrared Spectra of 1-Amino-1-deoxy-D-fructoses and 1-Glycino-1-deoxy-D-tagatose," Bull. Agr. Chem. Soc. Japan, vol. 24, No. 7,1960, pp. 703-710.

Petrie, E.M., "Biodegradable Polymers in Adhesive Systems," ASI, Jun. 1, 2007, Retrieved from the internet http://www.adhesivesmag.com/articles/print/biodegradable-polymers-in-adhesive-systems, Printed on Mar. 20, 2013, 8 pages.

Rai, U.S., et al, "Effect of polyacrylamide on the different properties of cement and mortar," Materials Science and Engineering: A, vol. 392, 2005, pp. 42-50.

(56) References Cited

OTHER PUBLICATIONS

Rinehart, K.L., et al, "Chemistry of the Neomycins. IV. Isolation of Neosamines B and C. Stereochemistry of Neobiosamine C," Journal of the American Chemical Society, vol. 80, Dec. 5, 1958, pp. 6461-6462.

Rinehart, K. L., et al, "Chemistry of the Neomycins. V. Differentiation of the Neomycin Complex. Identity of Framycetin and Neomycin B. Compounds Obtained from Methyl Neobiosaminide B," Journal of the American Chemical Society, vol. 82, Aug. 5, 1960, pp. 3938-3946.

Rinehart, K. L., et al, "Chemistry of the Neomycins. VI. Structure of Neobiosamine B," Journal of the American Chemistry Society, vol. 82, Jun. 5, 1960, pp. 2970-2971.

Rinehart, K. L., et al, "Chemistry of the Neomycins. VII. Compounds Obtained from Methyl Neobiosaminide C," Journal of the American Chemical Society, vol. 83, Feb. 5, 1961, pp. 643-648.

Rinehart, K. L., et al, "Identity of Neosamine C, "Diaminohexose II" From Zygomycin A, and 2,6- Diamino-2,6-Dideoxy-D-Glucose," Journal of the American Chemical Society, vol. 83, Jul. 5, 1961, pp. 2964-2965.

Rinehart, K. L., et al, "Biogenesis of the neomycins," Antimicrobial Agents and Chemotherapy 1961-1970, 1962, 1961, pp. 268-273.

Rodger, S.L., et al, "High Strength Cement Pastes," Journal of Materials Science, vol. 20, Aug. 1985, pp. 2853-2860.

Satoh, C., et al, "Studies on the Optical Rotatory Dispersion of Carbohydrate C-Nitroalcohols," Chemical & Pharmaceutical Bulletin, vol. 12, No. 4, 1964, pp. 518-520.

Sharples, A., "Structure and behavior of reverse osmosis membranes," Chemical Engineer (Rugby, United Kingdom), vol. 1, No. 257, 1972, pp. 34-37.

Smirnov, P.M., "The transformation of nitrogen compounds in peat-ammonium and peat-mineral fertilizers and the efficacy of these fertilizers," Izvestiya Timiryazevskoi Sel'skokhozyaistvennoi Akademii, vol. 6, 1964, pp. 72-85. (No English Translation Available).

Smith, L.V., "Synthesis of 2,6-diamino-2,6-dideoxy-D-galactose," 1967, 61 pages.

Smith, L.V., et al., "Amino sugar syntheses. X. Derivatives of benzyl 2-[(benzyloxycarbonyl)amino]-2-deoxy-3B1-Dgalactosiduronic acid and synthesis of 2,6-diamino-2,6-dideoxy-D-galactose," Justus Liebigs Annalen der Chemie, vol. 681, 1965, pp. 228-231. (English Translation Not Available).

Tanasescu, I. et al., "Photochemical reactions in the derivatives of o-nitrobenzylidene acetals. XIX. o-Nitrobenzylidene-myoinositol," Acad. Rep. Populare Romine, Filiala Cluj, Studii Cercetari Chim., vol. 13, No. 1, 1962, pp. 69-75.

Tsuji, K., et al, "Co-Irradiation as an Alternate Method for Sterilization of Penicillin G, Neomycin, Novobiocin, and Dihydrostreptomycin," Journal of Pharmaceutical Sciences, vol. 72, No. 1, Jan. 1983, pp. 23-26.

Tsunakawa, M., et al, "Inosamycin, A Complex of New Aminoglycoside Antibiotics. II. Structure Determination," Journal of Antibiotics, vol. 38, No. 10, Oct. 1985, pp. 1313-1321.

Usui, T., et al, "Synthesis of 3-O-Acetyl-2,6-Diazido-4-O-Benzyl-2,6-Dideoxy-L-Idopyranosyl Chloride, A Glycosyl Halide for the Synthesis of Neomycin B," Carbohydrate Research, vol. 130, 1984, pp. 165-177.

Valeriote, F.A., et al, "A Model for the Action of Vinblastine In Vivo," Biophysical Journal, vol. 6, 1966, pp. 145-152.

Weidmann, H., et al., "Derivatives of 2-amino-2-deoxy-D-glucopyranose. III. 2-Amino-3,4,6-tri-O-benzoyl-2-deoxy-1-thio-β-Dglucopyranosides," Justus Liebigs Annalen der Chemie, vol. 628, No. 1/3, 1959, pp. 255-256. (No English Translation Available).

Weidmann, H., et al., "Configuration of 2,6-diamino-2,6-dideoxyhexopyranose from neomycin C," Justus Liebigs Annalen der Chemie, vol. 644, 1961, pp. 127-129. (No English Translation Available).

Weidmann, H., et al., "Amino sugar syntheses. III. Synthesis of 2,6-diamino-2,6-dideoxy-D-glucopyranose," Justus Liebigs Annalen der Chemie, vol. 641, 1961, pp. 138-142. (No English Translation Available).

Weidmann, H., et al., "Amino sugar syntheses. II. Benzyl 2,6-diamino-2,6-dideoxy-α-D-glucopyranoside," Justus Liebigs Annalen der Chemie, vol. 641, 1961, pp. 132-137. (No English Translation Available).

Weidmann, H., et al., "Synthesis of 2,6-diamino-2,6-dideoxy-D-glucose," Angewandte Chemie, vol. 72, 1960, pp. 750. (No English Translation Available).

Wolfrom, M. L., et al, "2,6-Diamino-2,6-dideoxy-D-mannose Dihydrochloride," Chemical Communications, No. 8, 1965, pp. 143-144.

Wolfrom, M. L., et al, "Amino Derivatives of Starches. 2,6-Diamino-2,6-dideoxy-D-mannose Dihydrochloride," Journal of Organic Chemistry, vol. 30, Aug. 1965, pp. 2728-2731.

Wolfrom, M. L., et al, "Methyl 2-Deoxy-2-sulfoamino-β-D-glucopyranoside Trisulfate and the Preparation of Tri-O-acetyl-2-amino-2-deoxy-(-D-glucopyranosyl Bromide," Journal of Organic Chemistry, vol. 26, Jun. 1961, pp. 2145-2146.

Wolfrom, M. L., et al, "Synthesis of Amino Sugars by Reduction of Hydrazine Derivatives; D- and L-Ribosamine, D-Lyxosamine," Journal of the American Chemical Society, Jul. 20, 1959, vol. 81, pp. 3716-3719.

Zaidi, S. et al., "Preparation and determination of iron sucrate," Pakistan Journal of scientific and Industrial Research, vol. 6, 1963, pp. 114-115.

"COGNIS," accessed at https://web.archive.org/web/20120502131818/http://www.cognis.com/company/, accessed on Sep. 10, 2014, p. 1.

FDA "Part 872—Dental Devices, Subpart D—Prosthetic Devices, Sec. 872.3480 Polyacrylamide polymer (modified cationic) denture adhesive" Code of Federal Regulations, Title 21, vol. 8, accessed at https://web.archive.org/web/20100226140355/http://www.accessdata.fda.gov/scripts/cdrh/cfdocs/cfcfr/CFRSearch.cfm?fr=872.3480&SearchTerm=polyacrylamide, Apr. 1, 2009, p. 1.

FDA "Part 172—Food Additives Permitted for Direct Addition to Food for Human Consumption—Subpart C—Coatings, Films and Related Substances, Sec. 172.255 Polyacrylamide," Code of Federal Regulations, Tital 21, vol. 8, accessed at https://web.archive.org/web/20100226140038/http://www.accessdata.fda.gov/scripts/cdrh/cfdocs/cfcfr/CFRSearch.cfm?fr=172.255&SearchTerm=polyacrylamide, Apr. 1, 2009, p. 1.

European Commission "Opinion of the Scientific Committee on Cosmetic Products and Non-Food Products intended for Consumers concerning Acrylamide Residues in Cosmetics adopted by the plenary session of the SCCNFP of Sep. 30, 1999," accessed at https://web.archive,org/web/20120927233056/http://ec.europa.eu/health/scientific_committees/consumer_safety/opinions/sccnfp_opinions_97_04/sccp_out95 en.htm, accessed on Sep. 10, 2014, 2 pages.

Bahulekar, R. et al., "Polyacrylamides containing sugar residues: synthesis, characterization and hepatocyte attachment studies," Biotechnology Techniques, Oct. 1998, vol. 12, No. 10, pp. 721-724.

Bokhari, M., et al., "Emulsion-templated porous polymers as scaffolds for three dimensional cell culture: effect of synthesis parameters on scaffold formation and homogeneity," J. Mater. Chem., vol. 17, 2007, pp. 4088-4094.

Cameron, N. R., "High internal phase emulsion templating as a route to well-defined porous polymers," Polymer, vol. 46, Issue 5, Feb. 14, 2005, pp. 1439-1449.

Chalker-Scott, Linda, "The Myth of Polyacrylamide Hydrogels: Polyacrylamide hydrogels are environmentally safe substances that reduce irrigation needs," 2 pp., downloaded May 9, 2013 from http://www.theinformedgardener.com.

CID11032184—Compound Summary, Pub Chem Compound, NCBI, downloaded Apr. 2, 2013 from http://pubchem.ncbi.nlm.nih.gov/summary/summary.cgi?cid=11032184&loc=ec_res, pp. 1-3.

Dust Control on Military Helipads, downloaded from http://www.midwestind.com/problems-we-solve/controlling-dust/dust-control-on-military-helipads.html, accessed on Sep. 9, 2014, pp. 1-4.

(56) References Cited

OTHER PUBLICATIONS

Fanta, G.F. et al., "Graft Polymerization of Acrylamide and 2-Acrylamido-2-methylpropanesulfonic Acid," Journal of Applied Polymer Science, vol. 24, Issue 9, Nov. 1, 1979, pp. 2015-2023.
Final Office Action received for U.S. Appl. No. 13/879,976 dated Oct. 23, 2014.
Hill, T. G. et al., "Carbohydrate Protein Conjugates (CPC): The Design of New Materials to Stabilize Enzymes," Mat. Res. Symp. Proc., vol. 218, 1991, pp. 7-15.
International Search Report and Written Opinion for International Application No. PCT/US12/63211 mailed on Mar. 15, 2013.
International Search Report and Written Opinion for Intl. Pat. Appln. No. PCT/US2012/063240, mailed on Jan. 22, 2013, 9 pp.
International Search Report and Written Opinion received for PCT/US2012/067782 mailed Feb. 5, 2013.
Ivirico, J. L., et al., "Proliferation and differentiation of goat bone marrow stromal cells in 3D scaffolds with tunable hydrophilicity," Journal of Biomedical Materials Research, Part B: Applied Biomaterials, vol. 91, No. 1, 2009, pp. 277-286.
Moitessier, N., et al., "Orthogonally protected carbohydrate-based scaffolds," Tetrahedron Letters, vol. 46, Issue 37, Sep. 12, 2005, pp. 6191-6194.
Moshfeghian, A., et al., "Characterization of emulsified chitosan-PLGA matrixes formed using controlled-rate freezing and lyophilization technique," Journal of Biomedical Materials Research, Part A, vol. 79, No. 2, 2006, pp. 418-430.
Narayani, R., et al., "Collagen-poly (HEMA) hydrogels for the controlled delivery of methotrexate and cisplatin," International Journal of Pharmaceutics, vol. 138, 1996, pp. 121-124.
Non-final Office Action received for U.S. Appl. No. 13/879,976 dated Jul. 8, 2014.
Paterson, et al., "Carbohydrate-Based Crosslinking Agents: Potential Use in Hydrogels," Journal of Polymer Science Part A: Polymer Chemistry 2011, vol. 49, pp. 4312-4315.
Reti, Adrian R., et al., "Development of Urea-Based and Latex Emulsion Systems for Dust Control in Support of Military Operations," Jan. 1967, Pentagon Reports, Contract Report No. 3-172, Project No. 1-V-0-21701-A-046, Task 5, 70 pp.
Rushing, John F. et al., "Evaluation of Dust Palliatives for Unpaved Roads in Arid Climates," Aug. 2006, J. Pert Constr. Fac., pp. 281-286.
Storm Water Management Fact Sheet Dust Control, Environmental Protection Agency, Sep. 1999, EPA 832-F-99-003, 5 pp.
Suo, A., et al., "Synthesis and properties of carboxymethyl cellulose-graft-poly(acrylic acid-co-acrylamide) as a novel cellulose-based superabsorbent," Journal of Applied Polymer Science, vol. 103, Issue 3, Feb. 5, 2007, pp. 1382-1388.
Tingle, J. S., et al., "Evaluation of Expedient Methods for Mitigating Dust on Helipads," Dust Abatement Project, 2004, Final Report, ERDC/GSL TR-04-XX U.S. Army Corps of Engineers, 89 pp.
U.S. Environmental Protection Agency, "Chemical Summary for Acrylamide," prepared by Office of Pollution Prevention and Toxics, Sep. 1994, EPA 749-F-94-005a, 13 pages.
United States Department of Agriculture, Grain Inspection, Packers and Stockyards Administration, "2008 Annual Report of the Federal Grain Inspection Service," 57 pp.
Wang, Y., et al., "Fabrication and characterization of a PAM modified PHBV/BG scaffold," Chinese Science Bulletin, vol. 54, No. 17, 2009, pp. 2940-2946.
Yang, Y., et al., "Electrospun Composite Mats of Poly[(D,L-lactide)-co-glycolide] and Collagen with High Porosity as Potential Scaffolds for Skin Tissue Engineering," Macromolecular Materials and Engineering, vol. 294, No. 9, 2009, pp. 611-619.
Yu, Kai, et al., "Synthesis of Functional Polymer Brushes Containing Carbohydrate Residues in the hPyranose Form and Their Specific and Nonspecific Interactions with Proteins," 2010, Biomacromolecules, vol. 11, pp. 3073-3085.
Zhang, Y. et al., "Stimuli-responsive copolymers of n-isopropyl acrylamide with enhanced longevity in water for micro-and nanofluidics, drug delivery and non-woven applications," 2009, J. Mater. Chem. 19, pp. 4732-4739.
Aginsky Consulting Group, "Cosmetics Market Research Summary," Oct. 2007, pp. 1-8.
Badey et al., "Radically initiated polymerization of a methacryloylamido-terminated saccharide, 1, Monomer synthesis, homopolymerization and characterizations", Macromolecular Chemistry and Physics, 1996, vol. 197, p. 3711-3728.
Badey et al., "Radically initiated polymerization of a methacryloylamido-terminated saccharide, 2, Copolymerization with 2-hydroxyethyl methacrylate", Macromolecular Chemistry and Physics, 1997, vol. 198, p. 945-957.

\* cited by examiner e.g., 2,6-diamino-2,6-dideoxygalactose (D, L, or rac), 2,6-diamino-2,6-dideoxyglucose (D, L, or rac), etc.

HIGH PERFORMANCE ACRYLAMIDE ADHESIVES

CROSS-REFERENCE TO RELATED APPLICATIONS

This U.S. patent application is a U.S. National Phase Application under 35 U.S.C. §371 of International Application No. PCT/US2012/067765, filed on Dec. 4, 2012, the entire contents of which are incorporated herein by reference in their entirety for any and all purposes.

FIELD

The present technology is generally related acrylamide compounds as well as polymers, plastics, adhesives, and coatings prepared from acrylamide compounds and methods of making the acrylamide compounds and products prepared therefrom.

BACKGROUND

Polymeric materials derived from commonly employed monomers such styrene, α-olefins, acrylates, and the like generally display a low tendency to degrade over long periods of time. As such, polymeric materials in their various forms (e.g., plastics, adhesives, and coatings, etc.) may persist in the environment for potentially thousands of years. This waste not only takes up finite landfill space and contributes to unsightly flotillas of garbage in the world's oceans, but it also can have devastating impacts on surrounding ecosystem, such as through inadvertent ingestion of plastics by wildlife. Accordingly, there is considerable interest in the preparation of environmentally friendly, biocompatible, and non-accumulating polymeric materials which also display performance properties acceptable for a given application.

SUMMARY

The present technology provides acrylamide compounds which may be prepared from renewable resources such as sugars. The acrylamide compounds can be employed as monomers in the synthesis of polymeric materials. These polymers may be used in the preparation of plastics, adhesives, and coatings. Because of the nature of their chemical composition (e.g., sugars and sugar-like materials) such polymeric materials are subject to degradation upon long-term exposure to the natural environment. Accordingly, the polymeric materials are generally biocompatible and non-accumulating over time. Moreover, the present polymeric materials display excellent physical, chemical, and mechanical properties, and thus may have applications in numerous areas, including: curing agents; high-performance adhesives for wood, glass and metal; thermoplastics; thermosetting acrylics; thermosetting injection molded objects; coil coatings; hydrogels for tissue engineering and cell media; lithography, paper and label binding; and glass and plywood laminates.

In accordance with one aspect, the present technology provides compounds of Formula I:

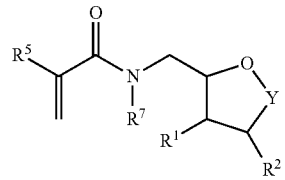

and stereoisomers thereof, where Y is —C(H)(R$^3$)— or —C(H)(R$^3$)—C(H)(R$^4$)—; R$^1$, R$^2$, R$^3$, and R$^4$ are independently an —OH, a protected hydroxyl group, or a group of Formula II:

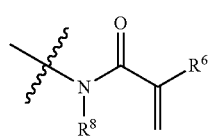

provided that not more than one of R$^1$, R$^2$, R$^3$, and R$^4$ is a group of Formula II; and R$^5$, R$^6$, R$^7$ and R$^8$ are each independently selected from hydrogen and a substituted or unsubstituted alkyl group. In some embodiments, the compounds of Formula I, Y is —C(H)(R$^3$)—C(H)(R$^4$)—. In some embodiments of the compounds of Formula I, the protecting group is selected from trimethylsilyl, t-butyldimethylsilyl, acetyl, benzyl, benzoyl, or methoxymethyl. In some embodiments of the compound of Formula I, one, two, three, or four of R$^1$, R$^2$, R$^3$, and R$^4$ are —OH. In certain embodiments, R$^1$, R$^2$, R$^3$, and R$^4$ are each an —OH, and the compound of Formula I has the Formula IA:

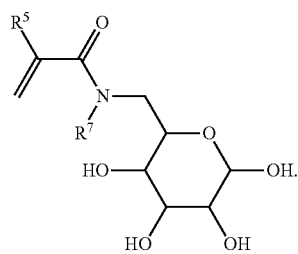

In some embodiments of compounds of Formula I, R$^5$ and R$^6$ are independently selected from the group consisting of H and a methyl group. In other embodiments of compounds of Formula I and IA, R$^5$ is H and in still others R$^5$ is methyl. In some embodiments of compounds of Formula I, R$^7$ and R$^8$ are independently selected from the group consisting of H, a methyl group and an ethyl group. In other embodiments of compounds of Formula I and IA, R$^7$ is H. Examples of compounds of Formula I or IA include but are not limited to N-((3,4,5,6-tetrahydroxytetrahydro-2H-pyran-2-yl)methyl) acrylamide or N-((3,4,5,6-tetrahydroxytetrahydro-2H-pyran-2-yl)methyl)methacrylamide.

In some embodiments of the compound of Formula I, one of R$^1$, R$^2$, R$^3$, and R$^4$ is the group of Formula II. In further embodiments, the compound of Formula I has a Formula IB:

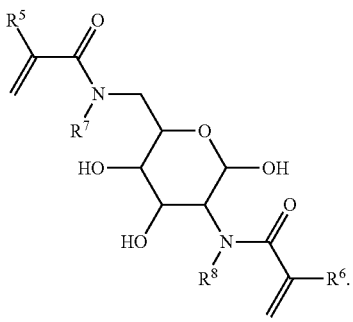

In some embodiments of compounds of Formula I and IB, $R^5$ and $R^6$ are independently selected from the group consisting of H and a methyl group. In others, $R^6$ is H and in still others $R^6$ is methyl. In still other embodiments, one of $R^5$ and $R^6$ is H and one is methyl. In other embodiments, both $R^5$ and $R^6$ are H or both are methyl. In some embodiments of compounds of Formula I and IB, $R^7$ and $R^8$ are independently selected from the group consisting of H, a methyl group and an ethyl group. In other embodiments, $R^7$ is H. In certain embodiments, $R^8$ is H. In some embodiments both $R^7$ and $R^8$ are H. Examples of compounds of Formula I or IB include but are not limited to N-((3,4,6-trihydroxy-5-methacrylamidotetrahydro-2H-pyran-2-yl)methyl)methacrylamide, N-((5-acrylamido-3,4,6-trihydroxytetrahydro-2H-pyran-2-yl)methyl)methacrylamide, N-(6-(acrylamidomethyl)-2,4,5-trihydroxytetrahydro-2H-pyran-3-yl)methacrylamide, or N-((5-acrylamido-3,4,6-trihydroxytetrahydro-2H-pyran-2-yl)methyl)acrylamide.

According to another aspect of the present technology, methods of making a compound of Formula I are provided. The methods include: contacting a compound of Formula III:

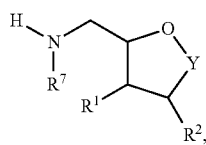

with a compound of Formula IV:

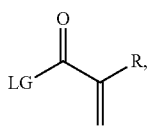

optionally in the presence of a base, where R is hydrogen or a substituted or unsubstituted alkyl group (e.g., a methyl group); Y is —C(H)($R^3$)— or —C(H)($R^3$)—C(H)($R^4$)—; $R^1$, $R^2$, $R^3$, and $R^4$ are independently an —OH, a protected hydroxyl group, or an —$NHR^8$, where $R^8$ is hydrogen or a substituted or unsubstituted alkyl group (e.g., a methyl group, or an ethyl group), provided that not more than one of $R^1$, $R^2$, $R^3$, and $R^4$ is an —$NHR^8$; $R^7$ is hydrogen or a substituted or unsubstituted alkyl group (e.g., a methyl group, or an ethyl group); and LG is a leaving group. In some embodiments, $R^7$ is hydrogen, $R^8$ is hydrogen or both $R^7$ and $R^8$ are hydrogen.

In some embodiments, LG is chloride. In some embodiments, the base is selected from pyridine, dimethylaminopyridine, triethylamine, diisopropylethylamine or a mixture of any two or more thereof.

Any of the compounds of the present technology may be employed as monomers to prepare polymers. Thus, according to another aspect, the present technology provides a polymer including one or more repeating units derived from the compound of Formula I:

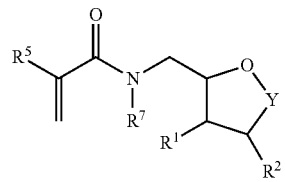

and stereoisomers thereof, where Y is —C(H)($R^3$)— or —C(H)($R^3$)—C(H)($R^4$)—; $R^1$, $R^2$, $R^3$, and $R^4$ are independently an —OH, a protected hydroxyl group, or a group of Formula II:

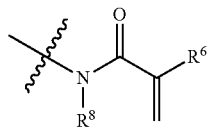

provided that not more than one of $R^1$, $R^2$, $R^3$, and $R^4$ is a group of Formula II; and $R^5$, $R^6$, $R^7$ and $R^8$ are independently selected from the group consisting of hydrogen and a substituted or unsubstituted alkyl group. In certain embodiments, $R^5$ and $R^6$ are independently selected from hydrogen or a methyl group. In some embodiments $R^7$ and $R^8$ are independently hydrogen, a methyl group, or an ethyl group. In certain embodiments, $R^7$ and $R^8$ are hydrogen. In some embodiments, $R^1$, $R^2$, $R^3$, and $R^4$ are each an —OH. In some embodiments, one of $R^1$, $R^2$, $R^3$, and $R^4$ is the group of Formula II.

The phrase "derived from" means that a polymer of the present technology is formed from, or otherwise prepared from, one or more compounds of Formula I, such as through a polymerization reaction. In this regard, one or more repeat units of the one or more compounds of Formula I will be incorporated into the present polymers. For example, and as will be appreciated by those of skill in the art, polymerization of one or more compounds of Formula I may provide a polymer which includes one or more of the following repeat units, where Y, $R^1$—$R^2$, $R^5$, and $R^7$ are defined as above:

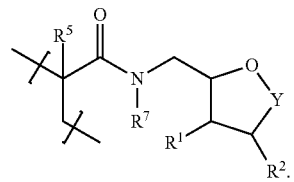

For clarity, it is understood that the above repeat unit may, but need not be, bonded it to itself. For example, where one or more compounds of Formula I are copolymerized with one or more other monomers (not of Formula I), the above repeating unit may or may not be separated by a repeating unit of the one or more other monomers, i.e., random, block, or alternating copolymers may be formed. In the case of a homopolymer derived of one compound of Formula I, or a copolymer derived from more than one compound of Formula I, such a repeat unit may be bonded to itself. As will also be appreciated by those of skill in the art, where the one or more compounds of Formula I include two acrylamide groups (i.e., where one of $R^1$, $R^2$, $R^3$, and $R^4$ is a group of Formula II), polymerization may proceed through either, or both, of the acrylamide groups.

In some embodiments, the polymer includes one or more repeating units derived from the compound of Formula IA, IB or both IA and IB (with variables defined as herein):

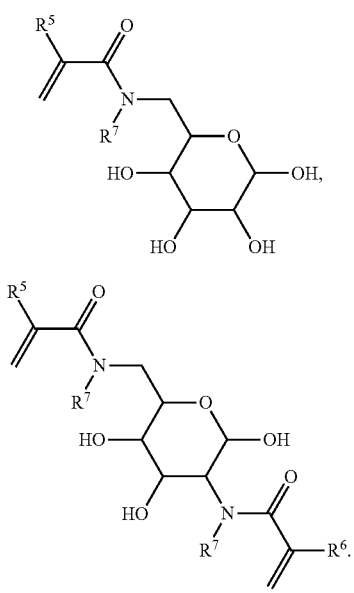

In some embodiments, the polymer includes one or more repeating units derived from one or more compounds selected from N-((3,4,5,6-tetrahydroxytetrahydro-2H-pyran-2-yl)methyl)acrylamide, N-((3,4,5,6-tetrahydroxytetrahydro-2H-pyran-2-yl)methyl)methacrylamide, N-((3,4,6-trihydroxy-5-methacrylamidotetrahydro-2H-pyran-2-yl)methyl)methacrylamide, N-((5-acrylamido-3,4,6-trihydroxytetrahydro-2H-pyran-2-yl)methyl)methacrylamide, N-(6-(acrylamidomethyl)-2,4,5-trihydroxytetrahydro-2H-pyran-3-yl)methacrylamide, or N-((5-acrylamido-3,4,6-trihydroxytetrahydro-2H-pyran-2-yl)methyl)acrylamide.

In some embodiments, the polymer includes from 2 to about 1,000,000 repeating units derived from the compound of Formula I. In some embodiments, any of the polymers described above may be a polyacrylamide, a polyacrylate, a polyvinyl, an epoxy, a polyurea, a polyurethane, an alkyd resin, or a copolymer of any of the foregoing. In other embodiments, any of the polymers described herein may include from about 0.2 wt % to 100% of one or more monomers of Formula I, IA, or IB. Examples of percentage weights of such monomers include 0.2, 0.3, 0.4, 0.5, 1, 2, 3, 4, 5, 6, 7, 8, 9, 10, 15, 20, 25, 30, 40, 50, 60, 70, 75, 80, 90, 95, 100, and ranges between and including any two such values.

According to another aspect, the present technology provides a coating or a plastic which includes any of the aforementioned polymers.

According to another aspect, an adhesive is provided, the adhesive including any of the aforementioned polymers. In some embodiments, the adhesive is a wood adhesive, a glass adhesive, a paper adhesive, or a metal adhesive. In some embodiments, the adhesive is a wood adhesive and the adhesive includes a polyacrylamide. In other embodiments, the adhesive is a paper adhesive and the adhesive includes a polyacrylate.

The foregoing summary is illustrative only and is not intended to be in any way limiting. In addition to the illustrative aspects, embodiments and features described above, further aspects, embodiments and features will become apparent by reference to the following drawings and the detailed description.

DETAILED DESCRIPTION

Figure 1:
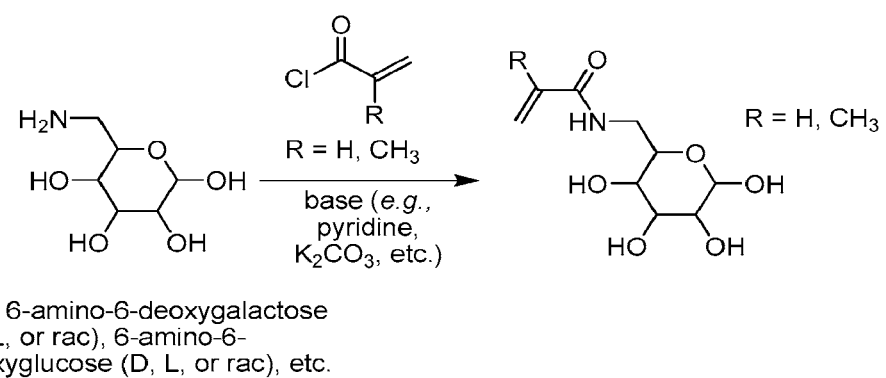
FIG. 1 is a schematic illustration of the preparation of N-((3,4,5,6-tetrahydroxytetrahydro-2H-pyran-2-yl)methyl)acrylamide and N-((3,4,5,6-tetrahydroxytetrahydro-2H-pyran-2-yl)methyl)methacrylamide, in an illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The technology is described herein using several definitions, as set forth throughout the specification.

The use of the terms "a" and "an" and "the" and similar referents in the context of describing the elements (especially in the context of the following claims) are to be construed to cover both the singular and the plural, unless otherwise indicated herein or clearly contradicted by context.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

In general, "substituted" refers to a group, as defined below (e.g., an alkyl or aryl group) in which one or more bonds to a hydrogen atom contained therein are replaced by a bond to non-hydrogen or non-carbon atoms or to carbon atoms bearing one or more heteroatoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, aroyloxyalkyl, heterocyclyloxy, and heterocyclylalkoxy groups; carbonyls (oxo), acyl; carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; thioamides; ureas; amidines; guanidines; enamines; imides; isocyanates; isothiocyanates; cyanates; thiocyanates; imines; nitro groups; nitriles; and the like. Such groups may be pendant or integral to the carbon chain itself. Cyclic groups (e.g., cycloalkyl, aryl, heterocyclyl) may also be substituted by carbon-based groups such as alkyl, alkenyl, and alkynyl, any of which may also be substituted (e.g., haloalkyl, hydroxyalkyl, aminoalkyl, haloalkenyl, and the like).

Alkyl groups include straight chain and branched alkyl groups having from 1 to 20 carbon atoms or, in some embodiments, from 1 to 12, 1 to 8, 1 to 6, or 1, 2, 3, or 4 carbon atoms. Alkyl groups further include cycloalkyl groups. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above. For example, the term haloalkyl refers to an alkyl group substituted with one or more halogen atoms.

Alkenyl groups include straight and branched chain and cycloalkyl groups as defined above, except that at least one double bond exists between two carbon atoms. Thus, alkenyl groups have from 2 to about 20 carbon atoms, and typically from 2 to 12 carbons or, in some embodiments, from 2 to 8, 2 to 6, or 2 to 4 carbon atoms. In some embodiments, alkenyl groups include cycloalkenyl groups having from 4 to 20 carbon atoms, 5 to 20 carbon atoms, 5 to 10 carbon atoms, or even 5, 6, 7, or 8 carbon atoms. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl, among others. Representative substituted alkenyl groups may be mono-substituted or substituted more than once, such as, but not limited to, mono-, di- or tri-substituted with substituents such as those listed above.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include mono-, bicyclic and polycyclic ring systems, such as, for example bridged cycloalkyl groups as described below, and fused rings, such as, but not limited to, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8, 2 to 6, or 2 to 4 carbon atoms. Examples include, but are not limited to —C≡CH, —C≡C(CH$_3$), —C≡(CH$_2$CH$_3$), —CH$_2$C≡CH, —CH$_2$C≡C(CH$_3$), and —CH$_2$C≡C(CH$_2$CH$_3$), among others. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthalenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 20 carbon atoms, 7 to 14 carbon atoms or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-ethyl-indanyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, heterocyclyl groups include 3 to 20 ring members, whereas other such groups have 3 to 6, 3 to 10, 3 to 12, or 3 to 15 ring members. Heterocyclyl groups encompass unsaturated, partially saturated and saturated ring systems, such as, for example, imidazolyl, imidazolinyl and imidazolidinyl groups. The phrase "heterocyclyl group" includes fused ring species including those including fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzothiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridyl, pyridazinyl, pyrimidinyl, pyrazinyl, thiophenyl, benzothiophenyl, furanyl, benzofuranyl, indolyl, azaindolyl (pyrrolopyridyl), indazolyl, benzimidazolyl, imidazopyridyl (azabenzimidazolyl), pyrazolopyridyl, triazolopyridyl, benzotriazolyl, benzoxazolyl, benzothiazolyl, benzothiadiazolyl, imidazopyridyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups. Although the phrase "heteroaryl groups" includes fused ring compounds such as indolyl and 2,3-dihydro indolyl, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

Alkoxy and aryloxy groups are hydroxyl groups (—OH) in which the bond to the hydrogen atom is replaced by a bond to a carbon atom of an alkyl group or aryl group, respectively, as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of aryloxy groups include but are not limited to phenoxy, naphthyloxy, and the like. Representative substituted alkoxy groups or aryloxy groups may be substituted one or more times with substituents such as those listed above.

Alkenoxy, alkynoxy, aralkyloxy, heterocyclyloxy, and heterocyclylalkoxy groups are defined analogously to alkoxy and aryloxy groups. Hence, alkenoxy, alkynoxy, aralkyloxy, heterocyclyloxy, and heterocyclylalkoxy groups are hydroxyl groups (—OH) in which the bond to the hydrogen atom is replaced by a bond to a carbon atom of, respectively, and alkene, alkyne, arylalkyl, heterocyclyl, or heterocyclylalkyl group as defined above. Representative substituted alkenoxy, alkynoxy, aralkyloxy, heterocyclyloxy, and heterocyclylalkoxy groups may be substituted one or more times with substituents such as those listed above.

The term "acrylamide group" or "acrylamido group" refers to RC(O)NR'— groups, where R is a substituted or unsubstituted alkenyl group as defined herein and R' is H, or a substituted or unsubstituted alkyl, alkenyl, or aryl group. Representative acrylamide groups include, but are not limited to $H_2C=CHC(O)NH—$, $H_2C=C(CH_3)C(O)NH—$, $H_2C=C(CH_2CH_3)C(O)NH—$, $H_3CCH=CHC(O)NH—$, and the like. The term "acrylamide group" specifically includes methacrylamide groups (and methacrylamido groups) such as $H_2C=C(CH_3)C(O)NH—$.

The term "acrylate reagent" refers to a reagent with the formula RC(O)-LG, where R is a substituted or unsubstituted alkenyl group as defined herein and LG is a leaving group as defined herein. Non-limiting examples of acrylate reagents include acryloyl chloride and methacryloyl chloride.

The term "acryloyl" or "acryl" refers to RC(O)— groups, where R is a substituted or unsubstituted alkenyl group as defined herein. Representative acryloyl groups include, but are not limited to $H_2C=CHC(O)—$, $H_2C=C(CH_3)C(O)—$, $H_2C=C(CH_2CH_3)C(O)—$, $H_3CCH=CHC(O)—$, and the like.

The term "acyl" refers to RC(O)— groups, where R is a substituted or unsubstituted alkyl group as defined herein. Representative acyl groups include, but are not limited to, acetyl ($CH_3C(O)—$), and the like.

The term "amine" (or "amino") as used herein refers to —NHR and —NRR' groups, wherein R, and R' are independently hydrogen, or a substituted or unsubstituted alkyl, alkenyl, alkynyl, aryl, or aralkyl group as defined herein. Non-limiting examples of amine groups include, but are not limited to, —$NH_2$, methylamino, dimethylamino, ethylamino, diethylamino, propylamino, isopropylamino, phenylamino, benzylamino, and the like.

The term "aroyl" refers to RC(O)— groups, where R is a substituted or unsubstituted aryl group as defined herein. Representative aroyl groups include, but are not limited to, benzoyl (PhC(O)—), and the like.

The term "base" refers to any chemical species, ionic or molecular, organic or inorganic, capable of accepting or receiving a proton (hydrogen ion) from another substance, generally an acid. The greater the tendency to accept a proton, the stronger the base. Representative bases include, but are not limited to: alkali or alkaline hydroxides (e.g., lithium hydroxide, sodium hydroxide, calcium hydroxide), hydrogencarbonates (e.g., sodium bicarbonate), carbonates (e.g., potassium carbonate), fluorides (e.g., potassium fluoride), alkoxides (e.g., sodium methoxide, potassium tert-butoxide), oxides (e.g., sodium oxide, magnesium oxide), hydrides (e.g., lithium hydride, calcium hydride), amides (e.g., sodium amide, lithium bis(trimethylsilylamide, lithium diisopropylamide)), alkyls (e.g., butyllithium, tert-butyllithium); ammonia; alkylamines (e.g., trimethylamine, triethylamine, diisopropylethylamine); pyridines (e.g., 2,6-dimethylaminopyridine, pyridine), phosphazenes, amidines, guanidines, and the like.

The term "carboxyl" (or "carboxylic acid") refers to —COOH.

The term "cyano" (or "nitrile") refers to —CN groups.

The term "ester" as used herein refers to —COOR groups, where R is a substituted or unsubstituted alkyl, alkenyl, alkynyl, or aryl group as defined herein.

The term "furanose" as used herein refers to carbohydrates and substituted derivatives of carbohydrates that include a tetrahydrofuran ring. Non-limiting examples of furanoses include, but are not limited to, arabinose, lyxose, ribose, xylose, and the like.

The term "halogen" (or "halo") refers to —F, —Cl, —Br, or —I groups.

The term "hydroperoxide" refers to —O—O—H groups.

The term "hydroxyl" (or "hydroxy") refers to —OH groups.

The term "hydroxyl protecting group" (or "hydroxy protecting group") signifies any group commonly used for the temporary protection of an —OH group, including but not limited to, alkoxycarbonyl, acyl, aroyl, alkylsilyl or alkylarylsilyl groups (hereinafter referred to simply as "silyl" groups), alkoxyalkyl, and arylmethyl groups. Alkoxycarbonyl protecting groups are alkyl-O—C(O)— groups such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. Alkoxyalkyl protecting groups are groups such as methoxymethyl, ethoxymethyl, methoxyethoxymethyl, or tetrahydrofuranyl and tetrahydropyranyl. Arylmethyl groups are groups such as benzyl and p-methoxybenzyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. Where multiple —OH groups are present, such groups may be protected as cyclic ethers, such as 1,3-dioxolanes and 1,3-dioxanes (e.g., acetonides). An extensive list of protecting groups for —OH groups may be found in Protective Groups in Organic Synthesis, Greene, T. W.; Wuts, P. G. M., John Wiley & Sons, New York, N.Y., (3rd Edition, 1999), which is hereby incorporated by reference in its entirety and for all purposes as if fully set forth herein.

The term "leaving group" or "LG" refers to groups readily displaceable by a nucleophile, such as an amine, alcohol, phosphorus, or thiol nucleophile or their respective anions. Such leaving groups are well known and include carboxylates, N-hydroxysuccinimide, N-hydroxybenzotriazole, halogen (halides), triflates, tosylates, mesylates, alkoxy, thioalkoxy, phosphinates, phosphonates, and the like. In addition, the term "leaving group" or "LG" is meant to encompass leaving group precursors (i.e., moieties that can easily be converted to a leaving group upon simply synthetic procedures such as alkylation, oxidation or protonation). Such leaving group precursors and methods for converting them to leaving groups are well known to those of ordinary skill in the art.

The term "peroxide" refers to —O—O— groups.

A "protected hydroxyl" group is an —OH group protected with a hydroxyl protecting group.

The term "pyranose" as used herein refers to carbohydrates and substituted derivatives of carbohydrates that include a tetrahydropyran ring. Non-limiting examples of pyranoses include, but are not limited to, glucose, galactose, idose, and the like.

The term "thio" (or "thioether" or sulfide) refer to —S— moieties, bonded to carbon atoms of other organic moieties.

The term "thiol" refers to —SH moieties.

Compounds of the present technology may be prepared through the functionalization of aminomethyl-substituted tetrahydropyran or aminomethyl-substituted tetrahydrofuran derivatives and salt forms thereof. In some embodiments, the aminomethyl-substituted tetrahydropyran or tetrahydrofuran derivatives have the Formula III as shown below:

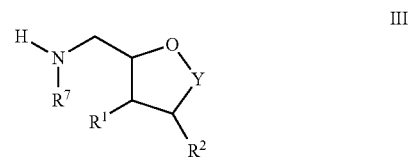

where Y is —C(H)(R$^3$)— or —C(H)(R$^3$)—C(H)(R$^4$)—; R$^1$, R$^2$, R$^3$, and R$^4$ are independently an —OH, a protected hydroxyl group, or an —NHR$^8$, where R$^8$ is hydrogen or a substituted or unsubstituted alkyl group (e.g., a methyl group, or an ethyl group), provided that not more than one of R$^1$, R$^2$, R$^3$, and R$^4$ is an —NHR$^8$, and R$^7$ is hydrogen or a substituted or unsubstituted alkyl group (e.g., a methyl group, or an ethyl group). Thus, the compounds of Formula III may be monoamino compounds or bis(amino) compounds. The compounds of Formula III may include protected hydroxyl groups, including but not limited to, silyloxy groups, esters, ethers, and the like. In this regard, the substituents R$^1$, R$^2$, R$^3$, and R$^4$ may independently be groups such as TMSO—, TBDMSO—, TBDPSO—, CH$_3$C(O)O—, CF$_3$C(O)O—, CH$_3$OCH$_2$O—, benzoyloxy, THPO— and the like. Furthermore, any two hydroxyl groups may be protected in the form of ring, such as a 1,3-dioxolane, 1,3-dioxane, 1,3,2-dioxasililane, or 1,3,2-dioxasilinane ring using reagents commonly known in the art (e.g., acetone, 2-methoxypropene, 2,2-dimethoxypropane, dihalodialkylsilanes, etc). Some compounds of Formula III are commercially available, such as 6-amino-6-deoxy-D-glucose hydrochloride (BOC Sciences, Shirey, N.Y.). Compounds of Formula III may also be prepared by known methods, such as from aldohexose or aldopentose sugars. Examples of such preparations include those disclosed by Keisuke, K. et al. in Makromolekulare Chemie (1986), 187, 1359-65, which is hereby incorporated by reference in its entirety and for all purposes as if fully set forth herein. Some examples of aldohexose and aldopentose sugars are shown below, as D-isomers, in pyranose and furanose form, respectively.

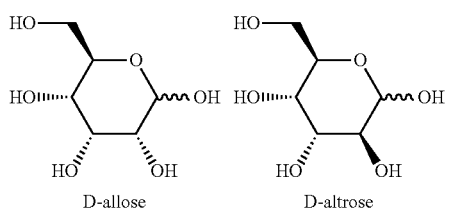

D-allose      D-altrose

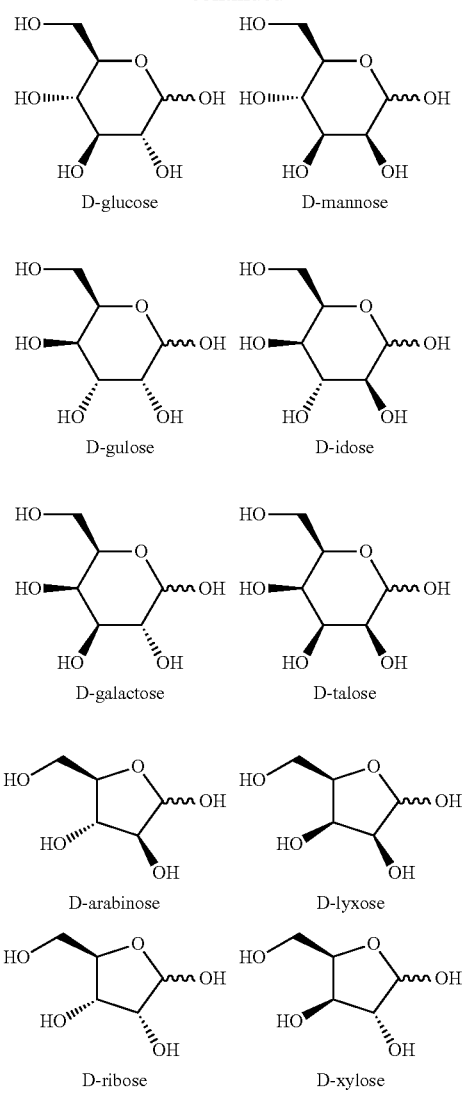

D-glucose
D-mannose
D-gulose
D-idose
D-galactose
D-talose
D-arabinose
D-lyxose
D-ribose
D-xylose The present technology contemplates the use of any stereoisomers of the compounds of Formula III. Further, there is no requirement that the compounds of Formula III be prepared from aldohexose or aldopentose sugars, such as those shown above. However, because of the ready availability of certain naturally-occurring sugars (e.g., D-glucose or D-galactose), it may be desired to prepare compounds of Formula III from such sugars simply for reasons of cost. Particularly useful compounds of Formula III include 6-(aminomethyl) tetrahydro-2H-pyran-2,3,4,5-tetraol (Formula IIIA) and 3-amino-6-(aminomethyl)tetrahydro-2H-pyran-2,4,5-triol (Formula IIIB) the structures of which are shown below.

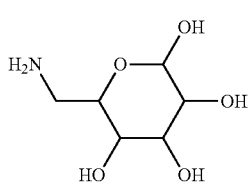

IIIA

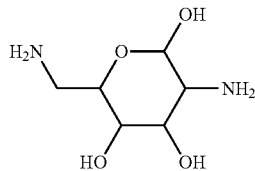

IIIB

The compound of Formula IIIA embraces such compounds as 6-amino-6-deoxy-D-glucose and 6-amino-6-deoxy-D-galactose, the use of which are described in Examples 1-3 and illustrated in FIG. 1. The compound of Formula IIIB embraces such compounds as 2,6-diamino-2,6-deoxy-D-glucose, and 2,6-diamino-2,6-dideoxy-D-galactose, the use of which are described in Examples 4-5 and illustrated in FIG. 2.

According to one aspect, the compound of Formula III is functionalized to provide a compound of Formula I, shown below:

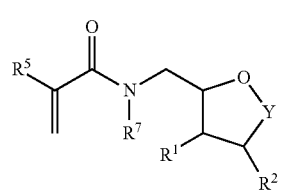

I and stereoisomers thereof, where Y is —C(H)($R^3$)— or —C(H)($R^3$)—C(H)($R^4$)—; $R^1$, $R^2$, $R^3$, and $R^4$ are independently an —OH, a protected hydroxyl group, or a group of Formula II:

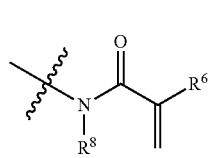

II provided that not more than one of $R^1$, $R^2$, $R^3$, and $R^4$ is a group of Formula II; $R^5$, $R^6$, $R^7$ and $R^8$ are independently selected from the group consisting of hydrogen and a substituted or unsubstituted alkyl group (e.g., a methyl group or an ethyl group). Thus, the compound of Formula I includes at least one acrylamide moiety.

The preparation of the compound of Formula I will typically be accomplished by contacting a compound of Formula III with an acrylate reagent, optionally in the presence of base. Acrylate reagents include, but are not limited to reagents such as acryloyl chloride and methacryloyl chloride. The amount of acrylate reagent used will generally be a stoichiometric amount, or a slight excess (such as about 1%, about 2%, about 3%, about 4%, about 5%, about 10%, about 25%, about 50%, or more than 50% excess), based upon the number of amino groups in the compound of Formula III. Typically, the reaction of the compound of Formula III with the acrylate reagent proceeds in good yield, with good levels of chemoselectivity, i.e., the more reactive amino groups are selectively functionalized in the presence of the hydroxyl groups, as to provide an acrylamide rather than an acrylate ester. In this regard, the functionalization reaction may proceed without the need for hydroxyl protecting groups, i.e., the hydroxyl groups of the compound of Formula III need not be protected. Where the hydroxyl groups of the compound of Formula III are protected, any suitable hydroxyl protecting groups may be used, including but not limited to, trimethylsilyl (TMS), t-butyldimethylsilyl (TBDMS), acetyl, benzyl (Bn), benzoyl (Bz), or methoxymethyl (MOM) protecting groups.

The functionalization of the compound of Formula III with the acrylate reagent optionally occurs in the presence of base. Non-aqueous reaction systems will typically employ a base, while biphasic aqueous reaction systems may not. As will be appreciated by those of skill in the art, a variety of bases may be used, including organic bases and inorganic bases. Examples of suitable organic bases include, but are not limited to pyridine, dimethylaminopyridine, triethylamine, and/or diisopropylethylamine. In the case of inorganic bases, it is generally preferred to select a base which will react with byproducts formed in the reaction but which will not react with the acrylate reagent (e.g., HCl when acryloyl or methacryloyl chloride are used). Examples of suitable inorganic bases include, but are not limited to alkali metal and alkaline metal carbonates (e.g., sodium carbonate, potassium carbonate, and the like) for a biphasic aqueous system or alkali metal hydrides, alkali earth metal hydrides, organometallics, such as n- or t-butyl lithium, and the like for a non-aqueous reaction system.

As will be appreciated by those of skill in the art, where a given compound of Formula III is available in salt form (including, but not limited to, a hydrochloride salt, hydrobromide salt, a sulfate or hydrogen sulfate salt, etc.), such a salt form may be neutralized or free-based with an organic or inorganic base prior to functionalization reaction with the acrylate reagent. In this regard, the base used to neutralize the salt may be the same or different from the optional base used in the functionalization of the compound of Formula III with the acrylate reagent.

A variety of classes of reaction solvents may be employed in the preparation of the compound of Formula I, including, but not limited to, water, alcohols, ethers, glycol ethers, esters, ketones, amides, nitriles, hydrocarbons, halogenated hydrocarbons, sulfoxides or mixtures of any two or more thereof. The reaction solvent may include, but is not limited to, water, methanol, ethanol, n-propanol, isopropanol, n-butanol, tert-butanol, diethyl ether, diisopropyl ether, dibutyl ether, tetrahydrofuran, 2-methyltetrahydrofuran, monoglyme, diglyme, ethyl acetate, acetone, 2-butanone, N,N-dimethylformamide, N,N-dimethylacetamide, N-methylpyrrolidinone, acetonitrile, hexane, toluene, xylenes, dichloromethane, chloroform or dimethyl sulfoxide. Alternatively, an organic base may be used as a solvent, e.g., pyridine or triethylamine. In some embodiments, even an organic carboxylic acid such as acetic acid may be used as the solvent.

The reaction of the compound of Formula III with the acrylate reagent and optional base and solvent(s) are performed at a temperature and for a time period sufficient to produce the compound of Formula I. In some embodiments, the reaction is performed at a temperature of about −30° C., about −20° C., about −10° C., about 0° C., about 10° C., about 20° C., or about 25° C., or ranges between any two of these values. In other embodiments, the reaction may be performed with heating. In this regard, the reaction may be performed at a temperature above room temperature, up to and including a refluxing temperature of the reaction mixture. The reaction may be performed at a temperature of about 25° C., about 30° C., about 40° C., about 50° C., about 60° C., about 70° C., about 80° C., about 90° C., about 100° C., about 120° C., about 140° C., about 160° C., about 180° C., about 200° C., about 220° C., about 240° C., about 260° C., about 280° C., or about 300° C., or ranges between any two of these values. The reaction may be performed for about 10 minutes to about 10 hours, about 30 minutes to about 10 hours, about 30 minutes to about 6 hours, about 10 minutes to about 8 hours, about 30 minutes to about 8 hours, about 1 hour to about 8 hours, about 3 hours to about 8 hours, about 4 hours to about 6 hours, or about 5 hours. The compound of Formula I thus prepared may optionally be purified by any number of methods known in the art, including but not limited to, chromatography, distillation, filtration, recrystallization, and the like. Alternatively, the compound of Formula I may be used directly in subsequent reaction without any substantial purification. The preparation of compounds with the Formula I are described in the Examples 1-5 and further illustrated in FIGS. 1-2.

The compound of Formula I includes one or two acrylamide groups. In this regard, the compound of Formula I may be used as a monomer to prepare polymers which include repeating units derived from the compound of Formula I. The compound of Formula I, or multiple compounds of Formula I may be polymerized with other monomers. For example, a single compound of Formula I may be polymerized in the absence of other monomers to give a polyacrylamide homopolymer. Multiple monomers with Formula I may be copolymerized to provide a polyacrylamide copolymer. Also, one or more compounds with Formula I may be copolymerized with other monomers to provide a polyacrylamide, a polyacrylate, a polyvinyl, an epoxy, a polyurea, a polyurethane, an alkyd resin, a polyester, a polyamide, a polyimide, or a copolymer of any of the foregoing. For example, a compound or multiple compounds of Formula I may be copolymerized with an acrylate monomer, a vinyl monomer, a stryrenic monomer, an epoxy-containing monomer, and the like.

Compounds of Formula I which include a single acrylamide group may be used as monomers and polymerized to provide thermoplastic polymers. An example of such a thermoplastic polymer is described in Example 6 and illustrated in FIG. 3. Compounds of Formula I with two acrylamide moieties may be polymerized to prepare thermosetting resins, capable of further cross-linking. An example of such a thermosetting polymer is described in Example 8.

Typically, the polymerization of the compound of Formula I will be initiated with the aid of an initiator, the selection of which will be determined based upon the identity of monomers used and the desired physical properties of the resultant polymer (e.g., molecular weight, viscosity, etc.). As used herein, the term "initiator" means a compound that includes at least one site from which a polymerization reaction can be initiated. Examples of suitable radical initiators include, but are not limited to: azo compounds (including, but not limited to, azobisisobutyronitrile (AIBN), azobiscyclohexanecarbonitrile (ABCN), and 2,2'-azobis 4-methoxy-2,4-dimethylvaleronitrile); acyl peroxides (including, but not limited to, peracetic acid, lauroyl peroxide); aroyl peroxides (including, but not limited to, benzoyl peroxide); alkyl peroxides (including, but not limited to, tert-butyl peroxide and dicumyl peroxide); alkyl hydroperoxides (including, but not limited to, cumene hydroperoxide), persulfates (including, but not limited to, ammonium persulfate, sodium persulfate, and potassium persulfate), acetophenones (including but not limited to acetophenone, 2,2-dimethoxy-2-phenyl acetophenone, 2-benzyl-2-(dimethylamino)-4'-morpholinobutyrophenone, 4'-tert-butyl-2',6'-dimethylacetophenone, 2,2-diethoxyacetophenone, 4'-ethoxyacetophenone, 3'-hydroxyacetophenone, 1-hydroxycyclohexyl phenyl ketone, 2-hydroxy-4'-(2-hydroxyethoxy)-2-methylpropiophenone, 2-methyl-4'-(methylthio)-2-morpholinopropiophenone, 4'-phenoxyacetophenone), benzils and benzoins (including but not limited to benzoin, benzoin ethyl ether, benzoin methyl ether, 4,4'-dimethoxybenzoin), benzophenones (including but not limited to benzophenone, benzophenone-3, 3',4,4'-tetracarboxylic dianhydride, 4-benzoylbiphenyl, 4,4'-bis(diethylamino)benzophenone, 4,4'-bis[2-(1-propenyl)phenoxy]benzophenone 4-(diethylamino)benzophenone, 4,4'-dihydroxybenzophenone, 4-(dimethylamino)benzophenone, 3,4-dimethylbenzophenone, 3- or 4-hydroxybenzophenone, 2-, 3-, or 4-methyl benzophenone, methyl benzoylformate, michler's ketone, quinones (including but not limited to anthraquinone-2-sulfonic acid, 2-tert-butylanthraquinone, 9,10-phenanthrenequinone, camphorquinone), and the like. The polymerization reaction may also be performed in any number of solvents or mixtures of solvents, such as those indicated for the preparation of the compound of Formula I. In certain embodiments, the polymerization reaction is performed in aqueous tetrahydrofuran. The polymerization reaction may be performed at a temperature of about 40° C., about 50° C., about 60° C., about 65° C., about 70° C., about 75° C., about 80° C., about 90° C., about 100° C., about 120° C., about 140° C., about 160° C., about 180° C., about 200° C., about 220° C., about 240° C., about 260° C., about 280° C., or about 300° C., or ranges between and including any two of these values. In certain embodiments, the polymerization reaction is performed at a temperature of about 60° C.

The polymers provided by the technology described herein may optionally be purified by methods known in the art. Such methods include, but are not limited to, purification by precipitation of the polymer from a solution of the polymer and/or by size exclusion chromatography. Furthermore, excess solvents, reactants, and by-products may be removed under reduced vacuum and/or by lyophilization.

The polymers of the present technology may include from 2 to about 1,000,000 repeating units derived from the compound of Formula I. In some embodiments, the polymers include 2 repeating units, about 5 repeating units, about 10 repeating units, about 50 repeating units, about 100 repeating units, about 500 repeating units, about 1,000 repeating units, about 5,000 repeating units, about 10,000 repeating units, about 50,000 repeating units, about 100,000 repeating units, about 200,000 repeating units, about 300,000 repeating units, about 400,000 repeating units, about 500,000 repeating units, about 600,000 repeating units, about 700,000 repeating units, about 800,000 repeating units, about 900,000 repeating units, about 1,000,000 repeating units derived from the compound of Formula I, or a range between and including any two of these values. In a certain embodiment, the polymer includes from about 5,000 to about 50,000 repeating units derived from the compound of Formula I.

The polymers of the present technology may have a molecular weight from about 500 to about 250,000,000 Daltons. In some embodiments, the polymers have a molecular weight of about 500 Daltons, about 1,250 Daltons, about 2,500 Daltons, about 12,500 Daltons, about 25,000 Daltons, about 125,000 Daltons, about 250,000 Daltons, about 1,250,000 Daltons, about 2,500,000 Daltons, about 12,500,000 Daltons, about 25,000,000 Daltons, about 50,000,000 Daltons, about 75,000,000 Daltons, about 100,000,000 Daltons, about, 125,000,000 Daltons, about 150,000,000 Daltons, about 175,000,000 Daltons, about 200,000,000 Daltons, about 225,000,000 Daltons, about 250,000,000 Daltons, or a range between and including any two of these values. In a certain embodiment, the polymer has a molecular weight from about 1,250,000 Daltons to about 12,500,000 Daltons.

In another embodiment, the polymer of the present technology has a molecular weight from about 700 Daltons to about 1,000,000 Daltons.

The polymers provided by the present technology are soluble in environmentally-friendly solvents, such as non-VOC (volatile organic compound(s)) solvents. In particular, the polymers are typically polar due to the presence of polar hydroxyl and amide groups, and as such, typically dissolve readily in water and polar organic solvents such as alcohols. Such solubility characteristics are useful in the preparation of water-borne adhesives and coatings. Furthermore, in contrast to most common organic polymers (e.g., polyacrylates, polystyrenes, polyvinyls, etc.), the polymers of the present technology are biocompatible and non-accumulating in the environment, since the polymers contain sugar or sugar-like moieties which can naturally be degraded over time (e.g., via metabolism by microorganisms). Thus, plastics, adhesives, and coatings prepared from such polymers display similar biocompatibility behavior.

Despite, the propensity of the present polymers toward degradation over long time-frames, the polymers display exceptional performance properties and are particularly well-suited for use in plastics and as adhesive and coating materials. For example, the present polymers may be used to prepare non-toxic plastic articles (e.g., plastic toys), with or without added plasticizers, pigments and other additives. Adhesives prepared from the present polymers typically display adhesions which meet or exceed about 600 psi (pounds per square inch), and thus can be classified as "high-performance" or "structural" adhesives. Without wishing to be bound by any particular theory, it is believed that the enhanced adhesion properties of the polymers, coatings, and adhesives of the present technology arise from the enhanced interaction of the polar nitrogen and hydroxyl functionality present in the polymers with various surfaces. In this regard, the polymers of the present technology may be used in coating materials, such as paints. Additionally, the present polymers, and adhesives prepared therefrom, exhibit excellent stability properties, including thermal stabilities greater than about 150° C., about 200° C., about 250° C., or about 300° C. The polymers of the present technology further display excellent miscibility and compatibility with many adhesive and coating resins. Many existing resins, including epoxy and isocyanate based resins, are susceptible to amine exudation and blush. In this process, low molecular weight amines migrate to the coating or adhesive surface, forming a greasy layer known as exudate. Such exudate is usually oily, impairing adhesion. Under high humidity conditions, the amine species at the coating or adhesive surface can react with carbon dioxide to form various carbonate and/or carbamate compounds, which also interfere with adhesion and further may give an unattractive appearance to the coated material. The humidity dependence on exudate formation can often prevent water-borne adhesives from being used with such resin based systems. The present polymers limit the formation of the exudate and improve adhesive and coating properties and allows for the formulation of water-borne adhesives. An example of the preparation of a water-borne adhesive described in Example 7 and illustrated in FIG. 4.

Adhesives and coatings of the present technology can be applied to a variety of substrates, including paper (e.g., labels, envelopes, and the like), cardboard, wood, glass, and metal such in a manner similar to that described by Krul, L. P. et al. in Macromolecular Chemistry and Polymeric Materials (2005), 78, 856-859 and by Nakanishi, G. et al. in the *Journal of Adhesion* (2008), 84, 638-652. Keisuke, K. et al. in Makromolekulare Chemie (1986), 187, 1359-65, each of which are hereby incorporated by reference in its entirety and for all purposes as if fully set forth herein. The adhesives and coatings may be applied as a pre-cured resins, or such resins may be cured thermally or with UV light after application to the substrate. As shown in Example 8, a two monomers with Formula I are copolymerized to give a polyacrylamide adhesive which is applied to a paper substrate (envelopes) and further cross-linked with UV light.

The present technology, thus generally described, will be understood more readily by reference to the following examples, which is provided by way of illustration and is not intended to be limiting of the present technology.

EXAMPLES

Example 1

Synthesis of a Galactose-Derived N-((3,4,5,6-tetrahydroxytetrahydro-2H-pyran-2-yl)methyl)acrylamide As shown in FIG. 1, an N-((3,4,5,6-tetrahydroxytetrahydro-2H-pyran-2-yl)methyl) acrylamide is generally synthesized by reaction of a 6-(aminomethyl)tetrahydro-2H-pyran-2,3,4,5-tetraol (or a salt form thereof) with acryloyl chloride in the presence of base. Analogous methacrylamide compounds are prepared using methacryloyl chloride. A galactose-derived N-((3,4,5,6-tetrahydroxytetrahydro-2H-pyran-2-yl)methyl)acrylamide is prepared as follows. Anhydrous tetrahydrofuran (500 mL) is added to a flame dried 1 L three neck flask and flooded with argon. To the tetrahydrofuran is added 30.0 g (139.5 mmol) of anhydrous 6-amino-6-deoxy-D-galactose hydrochloride and 31.2 g (394.4 mmol) anhydrous pyridine and allowed to dissolve at a temperature of −20° C. Then by drop-wise addition 13.1 g (140.5 mmol) of acryloyl chloride in 50 mL of dry tetrahydrofuran is added to the 6-amino-6-deoxy-D-galactose solution at room temperature followed by warming to 25° C. The reaction is allowed to proceed for five hours at 25° C. The pyridinium chloride is then removed by filtration followed by washing and the solvents removed by rotary evaporation and high vacuum to yield N-(6-deoxy-D-galactose)acrylamide, a galactose-derived N-((3,4,5,6-tetrahydroxytetrahydro-2H-pyran-2-yl) methyl)acrylamide. The reaction may also be performed using an equivalent molar amount of potassium carbonate as the base, in place of pyridine.

Example 2A

Alternative Synthesis of a Galactose-Derived N-((3,4,5,6-tetrahydroxytetrahydro-2H-pyran-2-yl)methyl) acrylamide

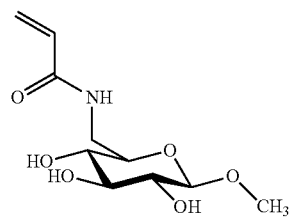

The synthesis of N-((3,4,5,6-tetrahydroxytetrahydro-2H-pyran-2-yl)methyl)acrylamide may also be accomplished using a biphasic reaction system. Anhydrous tetrahydrofuran (500 mL) is added to a flame dried 1 L three neck flask and flooded with argon. To water, 150 mL at 0° C., is added 30.0 g (139.5 mmol) of anhydrous 6-amino-6-deoxy-D-galactose hydrochloride and is neutralized with and 3.4 g (139.6 mmol) sodium hydroxide and allowed to dissolve. A solution of 13.1 g (140.5 mmol) of acryloyl chloride in 100 mL of methylene chloride is added to the 6-amino-6-deoxy-D-galactose ((2R, 3S,4S,5S)-6-(aminomethyl)tetrahydro-2H-pyran-2,3,4,5-tetraol) water solution at 0° C. and stirred rapidly to form an emulsion. Sodium hydroxide 1M solution is added dropwise to keep the mixture between a pH of 7-9. The reaction is allowed to proceed for five hours at 0° C. The stirring is then stopped and the phases are allowed to separate. The methylene chloride layer is extracted and the water layer is washed with three 25 mL portions of methylene chloride. The methylene chloride samples are combined, dried, and then the solvent is removed by rotary evaporation and high vacuum to yield N-(6-deoxy-D-galactose)acrylamide.

Example 2B

Synthesis of a Galactose-Derived N-(((3S,4S,5S, 6R)-3,4,5-trihydroxy-6-methoxytetrahydro-2H-pyran-2-yl)methyl)acrylamide The procedure of Example 2 was used with (3S,4S,5S,6R)-2-(aminomethyl)-6-methoxytetrahydro-2H-pyran-3,4,5-triol in place of 6-amino-6-deoxy-D-galactose to provide the title compound. $^1$H NMR: 8.22 ppm (1.01 H, t, amide), 6.32 ppm (1.00 H, m, vinyl), 6.07 ppm (0.99 H, d, vinyl), 5.57 ppm (1.04 H, d, vinyl), 4.6-5.2 ppm (2.82 H, b, OH), 4.52 ppm (1.19H, d, #1H), 3.61 ppm (2.00 H, m, #2H, #3H), 3.22 ppm (3.00 H, s, methoxy), 2.93 ppm (1.06H, t, #5H). The position-4 H (#4H) was under the water peak.

Example 3A

Synthesis of a Galactose-Derived N-((3,4,5,6-tetrahydroxytetrahydro-2H-pyran-2-yl)methyl)methacrylamide Using similar procedures as outlined in Example 1 or Example 2, 6-amino-6-deoxy-D-glucose is reacted with methacryloyl chloride to yield N-(6-deoxy-D-glucose)methacrylamide, a glucose-derived N-((3,4,5,6-tetrahydroxytetrahydro-2H-pyran-2-yl)methyl)methacrylamide.

Example 3B

Synthesis of a Glucose-Derived N-(((3S,4S,5S,6R)-3,4,5-trihydroxy-6-methoxytetrahydro-2H-pyran-2-yl)methyl)acrylamide

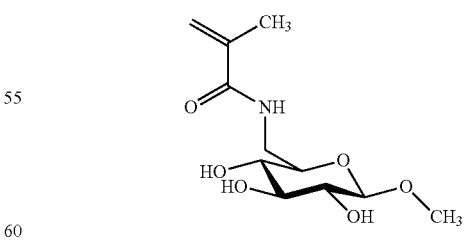

Using the procedure of Example 2, (3S,4S,5S,6R)-2-(aminomethyl)-6-methoxytetrahydro-2H-pyran-3,4,5-triol is reacted with methacryloyl chloride to yield the glucose-derived title compound. $^1$H NMR: 7.91 ppm (1.01 H, t, amide), 5.66 ppm (1.00H, s, vinyl), 5.32 ppm (1.07H, d, vinyl), 4.8-5.1 ppm (3.15 H, b, OH), 4.52 ppm (1.25 H, d, #1H), 3.44 ppm (2.00 H, m, #2H, #3H), 3.22 ppm (3.00 H, s, methoxy), 2.93 ppm (1.11 H, t, #5H). #4H was under the water peak. 1.86 (3.11H, s, acrylic methyl). High-resolution mass spectrometry: 284.1089 for M+Na$^+$.

Example 4

Figure 2:
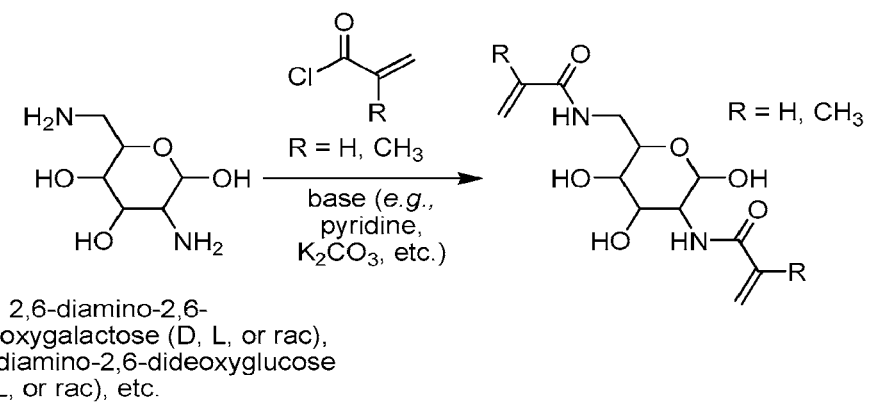
FIG. 2 is a schematic illustration of the preparation of N-((3,4,6-trihydroxy-5-methacrylamidotetrahydro-2H-pyran-2-yl)methyl)methacrylamide and N-((5-acrylamido-3,4,6-trihydroxytetrahydro-2H-pyran-2-yl)methyl)acrylamide, according to an illustrative embodiment.

Synthesis of a Glucose-Derived N-((3,4,6-trihydroxy-5-methacrylamidotetrahydro-2H-pyran-2-yl)methyl)methacrylamide Cross-Linking Agent As shown in FIG. 2, an N-((3,4,6-trihydroxy-5-methacrylamidotetrahydro-2H-pyran-2-yl)methyl)methacrylamide is generally synthesized by reaction of a 3-amino-6-(aminomethyl)tetrahydro-2H-pyran-2,4,5-triol (or a salt form thereof) with methacryloyl chloride in the presence of base. Acrylamides are prepared analogously using acryloyl chloride. In particular, a multi-functional cross-linking agent is prepared by the reaction of 2,6-diamino-2,6-dideoxy-D-glucose and methacryloyl chloride in the presence of an organic base. Anhydrous tetrahydrofuran (500 mL) is added to a flame dried 1 L three neck flask and flooded with argon. To the tetrahydrofuran is added 38.6 g (153.7 mmol) of 2,6-diamino-2,6-dideoxy-D-glucose hydrochloride and 32.5 g (411.3 mmol) pyridine and allowed to dissolve. Then by drop wise addition 33.2 g (317.4 mmol) of methacryloyl chloride in 55 mL of dry tetrahydrofuran is added to the 2,6-diamino-2,6-dideoxy-D-galactose solution at −20° C. followed by warming to room temperature. The reaction is allowed to proceed for five hours at room temperature. Pyridinium chloride is then removed by filtration followed by washing and the solvents removed by rotary evaporation and high vacuum to yield N,N-(2,6-deoxy-D-glucose)-2,6-methacrylamide, a glucose-derived N-((3,4,6-trihydroxy-5-methacrylamidotetrahydro-2H-pyran-2-yl)methyl)methacrylamide. The reaction may also be performed using an equivalent molar amount of potassium carbonate as the base, in place of pyridine.

Example 5

Synthesis of a Galactose-Derived N-((5-acrylamido-3,4,6-trihydroxytetrahydro-2H-pyran-2-yl)methyl)acrylamide Cross-linking Agent Using a similar procedure as outlined in Example 4 and shown in FIG. 2 (with either pyridine or potassium carbonate as base), 2,6-diamino-2,6-dideoxy-D-galactose is reacted with acryloyl chloride to yield N,N-(2,6-deoxy-D-galactose)-2,6-acrylamide, galactose-derived N-((5-acrylamido-3,4,6-trihydroxytetrahydro-2H-pyran-2-yl)methyl)acrylamide.

Example 6

Figure 3:
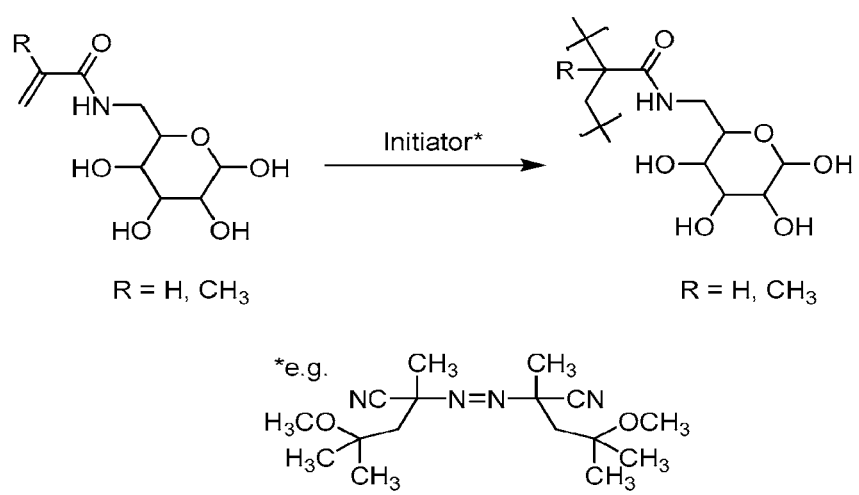
FIG. 3 is a schematic illustration of the preparation of poly(N-((3,4,6-trihydroxy-5-methacrylamidotetrahydro-2H-pyran-2-yl)methyl)methacrylamide) and poly(N-((5-acrylamido-3,4,6-trihydroxytetrahydro-2H-pyran-2-yl)methyl)acrylamide), according to an illustrative embodiment.

Synthesis of Galactose-Derived poly(N-((3,4,5,6-tetrahydroxytetrahydro-2H-pyran-2-yl)methyl)acrylamide Poly(N-((3,4,5,6-tetrahydroxytetrahydro-2H-pyran-2-yl)methyl)acrylamide (FIG. 3) is prepared as shown in FIG. 3. A galactose-derived poly(N-((3,4,5,6-tetrahydroxytetrahydro-2H-pyran-2-yl)methyl)acrylamide) may be prepared according to the following procedure. In a four-neck 500 mL separable flask equipped with a mechanical stirrer, a dropping funnel, and a condenser, N-(6-deoxy-D-galactose)acrylamide monomer (Example 1), 20 g; distilled water, 50 mL; and tetrahydrofuran, 150 mL, are added. The flask is warmed to 60° C. under air with stirring, and about 1 wt % of 2,2'-azobis (4-methoxy-2,4-dimethylvaleronitrile) is added as a polymerization initiator. The solution changed into a gel-like material in about 20 min. This point is tentatively taken as a standard for the end of reaction. Disappearance of monomer at this point can be confirmed by silica gel thin layer chromatography (TLC). After the reaction, the reaction mixture is concentrated under reduced pressure at room temperature, and remaining water in the viscous liquid is removed by freeze-drying to isolate poly(N-(6-deoxy-D-galactose)acrylamide), a galactose-derived poly(N-((3,4,5,6-tetrahydroxytetrahydro-2H-pyran-2-yl)methyl)acrylamide), as a white solid.

Example 7

Figure 4:
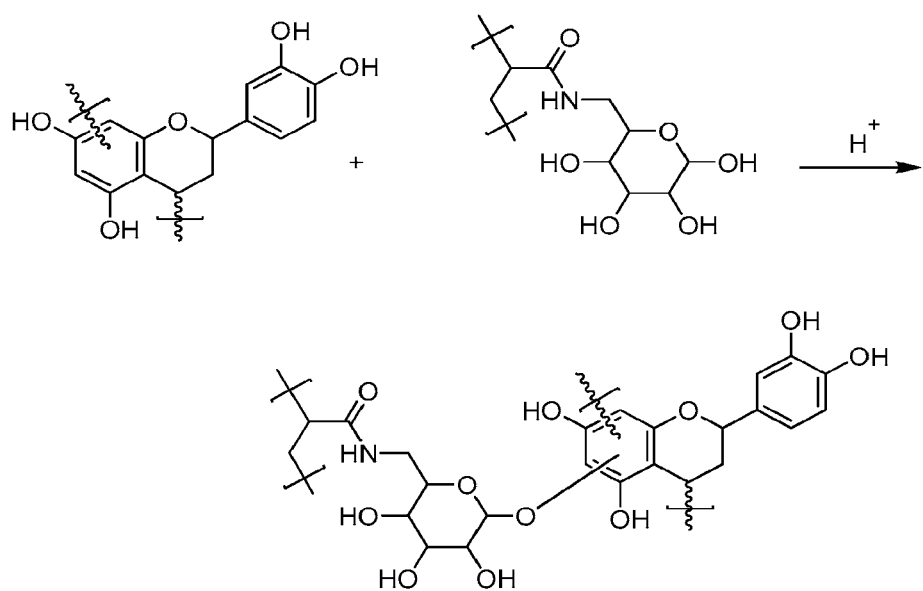
FIG. 4 is a schematic illustration of the acid-catalyzed curing of a wood adhesive containing tannin and poly(N-((3,4,5,6-tetrahydroxytetrahydro-2H-pyran-2-yl)methyl)acrylamide).

Formulation of a poly(N-((3,4,5,6-tetrahydroxytetrahydro-2H-pyran-2-yl)methyl)acrylamide)—Tannin Wood Adhesive A poly(N-((3,4,5,6-tetrahydroxytetrahydro-2H-pyran-2-yl)methyl)acrylamide)-tannin adhesive is prepared using equal amounts of the galactose-derived poly(N-((3,4,5,6-tetrahydroxytetrahydro-2H-pyran-2-yl)methyl)acrylamide) prepared in Example 6 and tannin as aqueous solutions at room temperature. The total concentration of organic solids in the adhesive formulation is adjusted to 57% with distilled water. A 1 mL aliquot of 0.5-1M solution of ammonium chloride, sulfuric acid, or p-toluenesulfonic acid is used as a curing agent. The curing process is shown in FIG. 4.

Example 8

Preparation of a poly(N-((3,4,5,6-tetrahydroxytetrahydro-2H-pyran-2-yl)methyl)acrylamide-co-N-((3,4,6-trihydroxy-5-methacrylamidotetrahydro-2H-pyran-2-yl)methyl)methacrylamide) Adhesive for Label and/or Envelope Applications In a four-neck 500 mL separable flask equipped with a mechanical stirrer, a dropping funnel, and a condenser, N-(6-deoxy-D-glucose)acrylamide monomer (Example 1), 60 g, and distilled water, 50 mL are added. To this is added 2 g of N,N-(2,6-deoxy-D-glucose)-2,6-methacrylamide (Example 4). The flask is gently warmed up to 60° C. under air with stirring, and 0.6 g of DAROCUR 1173 (2-hydroxy-2-methylpropiophenone, available from BASF) is added as a polymerization initiator.

The above polymeric adhesive may be applied to labels or envelopes (or other backing material), as a viscous solution, and further cured (cross-linked) with UV light. After drying, the polymer can be tackified with a moisture source and then the label adhered to the surface of choice.

EQUIVALENTS

The embodiments, illustratively described herein may suitably be practiced in the absence of any element or elements, limitation or limitations, not specifically disclosed herein. Thus, for example, the terms 'comprising,' 'including,' 'containing,' etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase 'consisting essentially of' will be understood to include those elements specifically recited and those additional elements that do not materially affect the basic and novel characteristics of the claimed technology. The phrase 'consisting of' excludes any element not specified.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent compositions, apparatuses, and methods within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as 'up to,' 'at least,' 'greater than,' 'less than,' and the like, include the number recited and refer to ranges which can be subsequently broken down into subranges as discussed above. Finally, as will be understood by one skilled in the art, a range includes each individual member.

While certain embodiments have been illustrated and described, it should be understood that changes and modifications can be made therein in accordance with ordinary skill in the art without departing from the technology in its broader aspects as defined in the following claims.

What is claimed is:

1. A compound of Formula I:

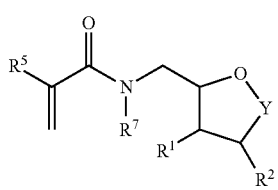

and stereoisomers thereof, wherein
Y is —C(H)(R³)— or —C(H)(R³)—C(H)(R⁴)—;
R¹, R², R³, and R⁴ are independently an —OH, a protected hydroxyl group, or a group of Formula II:

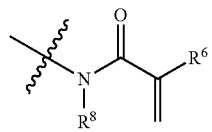

wherein one of R¹, R², R³, and R⁴ is a group of Formula II; and
R⁵, R⁶, R⁷ and R⁸ are independently selected from hydrogen and a substituted or unsubstituted alkyl group.

2. The compound of claim 1 wherein the protected hydroxyl group is selected from trimethylsilyl, t-butyldimethylsilyl, acetyl, benzyl, benzoyl, or methoxymethyl.

3. The compound of claim 1 wherein R⁵ and R⁶ are independently selected from the group consisting of H and a methyl group.

4. The compound of claim 1 wherein R⁷ and R⁸ are independently selected from the group consisting of H, a methyl group and an ethyl group.

5. The compound of claim 1 having Formula IB:

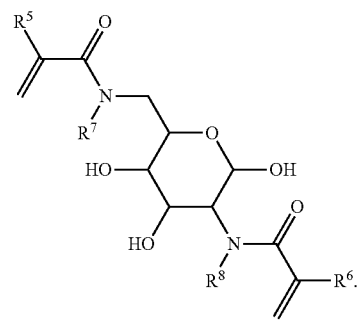

6. The compound of claim 1 selected from
N-((3,4,6-trihydroxy-5-methacrylamidotetrahydro-2H-pyran-2-yl)methyl)methacrylamide,
N-((5-acrylamido-3,4,6-trihydroxytetrahydro-2H-pyran-2-yl)methyl)methacrylamide,
N-(6-(acrylamidomethyl)-2,4,5-trihydroxytetrahydro-2H-pyran-3-yl)methacrylamide, or
N-((5-acrylamido-3,4,6-trihydroxytetrahydro-2H-pyran-2-yl)methyl)acrylamide.

7. A polymer comprising one or more repeating units derived from the compound of Formula I:

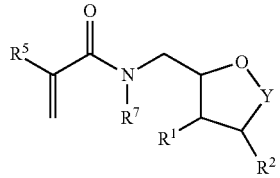

and stereoisomers thereof, wherein
Y is —C(H)(R³)— or —C(H)(R³)—C(H)(R⁴)—;
R¹, R², R³, and R⁴ are independently an —OH, a protected hydroxyl group, or a group of Formula II:

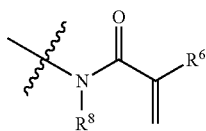

wherein one of $R^1$, $R^2$, $R^3$, and $R^4$ is a group of Formula II; and
$R^5$, $R^6$, $R^7$ and $R^8$ are independently selected from the group consisting of hydrogen and a substituted or unsubstituted alkyl group.

8. The polymer of claim 7 wherein $R^5$ and $R^6$ are independently selected from the group consisting of H and a methyl group.

9. The polymer of claim 7 wherein $R^7$ and $R^8$ are independently selected from the group consisting of H, a methyl group and an ethyl group.

10. The polymer of claim 7 wherein the one or more repeating units are derived from the compound of Formula IB:

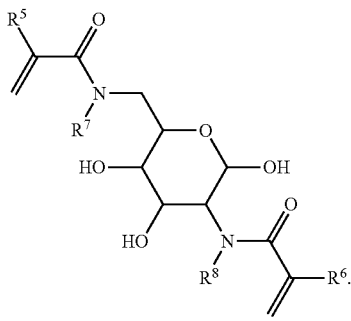

11. The polymer of claim 7 wherein the one or more repeating units are derived from one or more compounds selected from
N-((3,4,6-trihydroxy-5-methacrylamidotetrahydro-2H-pyran-2-yl)methyl)methacrylamide,
N-((5-acrylamido-3,4,6-trihydroxytetrahydro-2H-pyran-2-yl)methyl)methacrylamide,
N-(6-(acrylamidomethyl)-2,4,5-trihydroxytetrahydro-2H-pyran-3-yl)methacrylamide, or
N-((5-acrylamido-3,4,6-trihydroxytetrahydro-2H-pyran-2-yl)methyl)acrylamide.

12. The polymer of claim 7 comprising from 2 to about 1,000,000 repeating units derived from the compound of Formula I.

13. The polymer of claim 7 selected from a polyacrylamide, a polyacrylate, a polyvinyl, an epoxy, a polyurea, a polyurethane, an alkyd resin, or a copolymer of any of the foregoing.

14. A method of making a compound of Formula I comprising:
contacting a compound of Formula III,

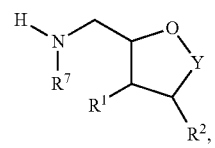

with a compound of Formula IV,

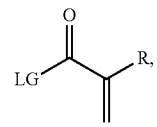

optionally in the presence of a base, wherein
R is hydrogen or a substituted or unsubstituted alkyl group;
Y is —C(H)($R^3$)— or —C(H)($R^3$)—C(H)($R^4$)—;
$R^1$, $R^2$, $R^3$, and $R^4$ are independently an —OH, a protected hydroxyl group, or an —$NHR^8$ wherein $R^8$ is hydrogen or a substituted or unsubstituted alkyl group, wherein one of $R^1$, $R^2$, $R^3$, and $R^4$ is an —$NHR^8$;
$R^7$ is hydrogen or a substituted or unsubstituted alkyl group; and
LG is a leaving group.

15. The method of claim 14 wherein the protected hydroxyl group is selected from trimethylsilyl, t-butyldimethylsilyl, acetyl, benzyl, benzoyl, or methoxymethyl.

16. The method of claim 14 wherein $R^7$ and $R^8$ are hydrogen.

17. The method of claim 15 wherein LG is chloride, and the base is selected from pyridine, dimethylaminopyridine, triethylamine, diisopropylethylamine or a mixture of any two or more thereof.

* * * * *

UNITED STATES PATENT AND TRADEMARK OFFICE
CERTIFICATE OF CORRECTION

| | | |
|---|---|---|
| PATENT NO. | : 9,212,245 B2 | Page 1 of 1 |
| APPLICATION NO. | : 13/980535 | |
| DATED | : December 15, 2015 | |
| INVENTOR(S) | : Carlson et al. | |

It is certified that error appears in the above-identified patent and that said Letters Patent is hereby corrected as shown below:

In Column 1, Line 8, delete "This U.S." and insert -- This --, therefor.

In Column 1, Line 9, delete "§371" and insert -- § 371 --, therefor.

In Column 21, Line 49, delete "galactose-derived" and insert -- a galactose-derived --, therefor.

Signed and Sealed this
Twenty-fourth Day of May, 2016

Michelle K. Lee
*Director of the United States Patent and Trademark Office*